(12) United States Patent
Ozawa et al.

(10) Patent No.: US 6,967,673 B2
(45) Date of Patent: Nov. 22, 2005

(54) ELECTRONIC ENDOSCOPE SYSTEM WITH COLOR-BALANCE ALTERATION PROCESS

(75) Inventors: Ryo Ozawa, Saitama (JP); Mikihito Kimishima, Saitama (JP)

(73) Assignee: PENTAX Corporation, Tokyo (JP)

( * ) Notice: Subject to any disclaimer, the term of this patent is extended or adjusted under 35 U.S.C. 154(b) by 446 days.

(21) Appl. No.: 10/178,758

(22) Filed: Jun. 25, 2002

(65) Prior Publication Data
US 2003/0030722 A1    Feb. 13, 2003

(30) Foreign Application Priority Data
Jun. 26, 2001 (JP) ............................ P2001-193308

(51) Int. Cl.⁷ .............................................. H04N 7/18
(52) U.S. Cl. ....................................................... 348/71
(58) Field of Search .............................. 348/45, 65–72; 600/101, 109, 113, 168; 606/14; H04N 7/18

(56) References Cited

U.S. PATENT DOCUMENTS

| | | | |
|---|---|---|---|
| 4,780,762 A * | 10/1988 | Nagasaki | 348/45 |
| 4,831,437 A * | 5/1989 | Nishioka et al. | 348/71 |
| 5,398,056 A * | 3/1995 | Yabe et al. | 348/68 |
| 5,864,361 A | 1/1999 | Sekiya et al. | |
| 5,929,899 A | 7/1999 | Takahashi et al. | |
| 6,025,873 A * | 2/2000 | Nishioka et al. | 348/72 |
| 6,371,908 B1 | 4/2002 | Furusawa et al. | |
| 2001/0041887 A1* | 11/2001 | Crowley | 606/14 |
| 2001/0052929 A1* | 12/2001 | Abe | 348/65 |

FOREIGN PATENT DOCUMENTS

JP    2001-25025    1/2001

\* cited by examiner

*Primary Examiner*—Richard Lee
(74) *Attorney, Agent, or Firm*—Greenblum & Bernstein, P.L.C.

(57) ABSTRACT

An electronic endoscope system includes a video scope having a solid-state image sensor for successively producing a frame of color image-pixel signals, and an image-signal processor for producing a color video signal based on the frame of color image-pixel signals. A calculation system calculates a difference value between a value of a central single-color image-pixel signal and an average of values of one selected from single-color image-pixel signals surrounding the central single-color image-pixel signal. A color-balance alteration system alters the value of the central single-color image-pixel signal based on the difference value calculated by the calculation system. A selection system performs the selection of the circumferential image-pixel signals such that the circumferential image-pixel signals to be selected are farther from the central image-pixel signal, as a spatial frequency of an endoscope image to be reproduced based on the color video signals is lower.

15 Claims, 28 Drawing Sheets

FIG. 5

| $R_{(i-3)(j-3)}$ | $R_{(i-3)(j-2)}$ | $R_{(i-3)(j-1)}$ | $R_{(i-3)j}$ | $R_{(i-3)(j+1)}$ | $R_{(i-3)(j+2)}$ | $R_{(i-3)(j+3)}$ |
|---|---|---|---|---|---|---|
| $R_{(i-2)(j-3)}$ | $R_{(i-2)(j-2)}$ | $R_{(i-2)(j-1)}$ | $R_{(i-2)j}$ | $R_{(i-2)(j+1)}$ | $R_{(i-2)(j+2)}$ | $R_{(i-2)(j+3)}$ |
| $R_{(i-1)(j-3)}$ | $R_{(i-1)(j-2)}$ | $R_{(i-1)(j-1)}$ | $R_{(i-1)j}$ | $R_{(i-1)(j+1)}$ | $R_{(i-1)(j+2)}$ | $R_{(i-1)(j+3)}$ |
| $R_{i(j-3)}$ | $R_{i(j-2)}$ | $R_{i(j-1)}$ | $R_{ij}$ | $R_{i(j+1)}$ | $R_{i(j+2)}$ | $R_{i(j+3)}$ |
| $R_{(i+1)(j-3)}$ | $R_{(i+1)(j-2)}$ | $R_{(i+1)(j-1)}$ | $R_{(i+1)j}$ | $R_{(i+1)(j+1)}$ | $R_{(i+1)(j+2)}$ | $R_{(i+1)(j+3)}$ |
| $R_{(i+2)(j-3)}$ | $R_{(i+2)(j-2)}$ | $R_{(i+2)(j-1)}$ | $R_{(i+2)j}$ | $R_{(i+2)(j+1)}$ | $R_{(i+2)(j+2)}$ | $R_{(i+2)(j+3)}$ |
| $R_{(i+3)(j-3)}$ | $R_{(i+3)(j-2)}$ | $R_{(i+3)(j-1)}$ | $R_{(i+3)j}$ | $R_{(i+3)(j+1)}$ | $R_{(i+3)(j+2)}$ | $R_{(i+3)(j+3)}$ |

FIG. 7

FACTOR-SETTING TABLE

|  | DISTANCE | 1st. MODE | 2nd. MODE | 3rd. MODE | 4th. MODE | 5th. MODE | 6th. MODE | 7th. MODE | 8th. MODE |
|---|---|---|---|---|---|---|---|---|---|
| f01 | 0 | 1 | 1 | 1 | 1 | 1 | 1 | 1 | 1 |
| f02 | 1*d | -1/4 | 0 | 0 | 0 | 0 | 0 | 0 | 0 |
| f03 | 1.41*d | 0 | -1/4 | -1/8 | 0 | 0 | 0 | 0 | 0 |
| f04 | 2*d | 0 | 0 | -1/8 | -1/12 | 0 | 0 | 0 | 0 |
| f05 | 2.24*d | 0 | 0 | 0 | -1/12 | -1/12 | 0 | 0 | 0 |
| f06 | 2.83*d | 0 | 0 | 0 | 0 | -1/12 | -1/8 | 0 | 0 |
| f07 | 3*d | 0 | 0 | 0 | 0 | 0 | -1/8 | 0 | 0 |
| f08 | 3.16*d | 0 | 0 | 0 | 0 | 0 | 0 | -1/16 | 0 |
| f09 | 3.61*d | 0 | 0 | 0 | 0 | 0 | 0 | -1/16 | 0 |
| f10 | 4.24*d | 0 | 0 | 0 | 0 | 0 | 0 | 0 | -1/4 |

FIG. 8

FACTOR-SETTING-MODE SELECTION TABLE

| MAGNIFYING-POWER | 1 | 2 | 3 | 4 |
|---|---|---|---|---|
| VIDEO SCOPE 10' (M×N) | 1st. MODE | 3rd. MODE | 5th. MODE | 7th. MODE |
| VIDEO SCOPE 10 (m×n) | 2nd. MODE | 4th. MODE | 6th. MODE | 8th. MODE |

FIG. 27

FACTOR-SETTING-MODE SELECTION TABLE

| MAGNIFYING-POWER | 1>mp>1.5 | 1.5>mp>2.5 | 2.5>mp>3.5 | 3.5>mp>4 |
|---|---|---|---|---|
| VIDEO SCOPE 10'<br>(M×N) | 1st. MODE | 3rd. MODE | 5th. MODE | 7th. MODE |
| VIDEO SCOPE 10<br>(m×n) | 2nd. MODE | 4th. MODE | 6th. MODE | 8th. MODE |

FIG. 30

FACTOR-SETTING-MODE SELECTION TABLE

| OPENING VALUE | $OV_{MIN} \leq ov < OV_1$ | $OV_1 \leq ov < OV_2$ | $OV_2 \leq ov < OV_2$ | $OV_2 \leq ov$ |
|---|---|---|---|---|
| VIDEO SCOPE 10' (M×N) | 1st. MODE | 3rd. MODE | 5th. MODE | 7th. MODE |
| VIDEO SCOPE 10 (m×n) | 2nd. MODE | 4th. MODE | 6th. MODE | 8th. MODE |

ELECTRONIC ENDOSCOPE SYSTEM WITH COLOR-BALANCE ALTERATION PROCESS

BACKGROUND OF THE INVENTION

1. Field of the Invention

The present invention relates to an electronic endoscope system in which an endoscope image is reproduced as a full color image on a TV monitor, and, in particular, to such an electronic endoscope system with a simulated dye-spraying process or color-balance alteration process, which is constituted such that the endoscope image can be reproduced on the TV monitor as if it were sprayed with a dye-solution.

2. Description of the Related Art

As is well known, an electronic endoscope system includes a video scope, inserted in an organ of a human body, having a solid-state image sensor for capturing an organ image or endoscope image as a frame of image-pixel signals, an image-signal processing unit for producing a video signal based on the frames of image-pixel signals successively read from the solid-state image sensor, and a TV monitor for reproducing the endoscope image as a motion picture based on the video signal fed from the image-signal processing unit.

Recently, it is usual to manufacture an electronic endoscope system such that the endoscope image is reproduced as a full color motion image on a TV monitor. Thus, a dye-spraying examination method was developed and has been used as a medical examination method in the medical field in which electronic endoscope systems are used. For example, when a subtle uneven surface of the mucous membrane of a stomach or a colon is examined, the dye-spraying medical method is utilized.

In particular, the mucous membrane surface of the stomach or the colon features a reddish orange tone as a whole, and thus it is very difficult to examine the subtle unevenness of the mucous membrane surface. In order that the subtle unevenness of the mucous membrane surface can be clearly and easily examined on a TV monitor, a bluish solution, such as an Indigo Carmine solution, is introduced into a forceps-insertion passage of the video scope, and is sprayed over the mucous membrane surface. The solution has a tendency toward gathering at fine recess areas on the mucous membrane surface, and it flows away from fine land areas on the mucous membrane surface. Namely, the fine recess areas on the mucous membrane surface are colored blue, and clearly contrast with the reddish orange areas. Thus, it is possible to easily carry out an examination of the subtle unevenness of the mucous membrane surface.

However, there are various drawbacks in the dye-spraying medical examination method. For example, a dye must be harmless to a human body, and it is troublesome to develop a harmless dye. Also, an introduction of a dye-spraying medical examination method prolongs the medical examination time when using the electronic endoscope system, resulting in an increase in the patient's pain. Further, once a dye-solution is sprayed, it is impossible to immediately reproduce an endoscope image without the sprayed dye-solution.

In order to settle the above-mentioned problems, Japanese Laid-Open Patent Publication (KOKAI) No. 2001-25025 discloses an electronic endoscope system with a simulated dye-spraying process for electronically processing an endoscope image as if it were sprayed with a blue-solution.

In this electronic endoscope system, a full color endoscope image is formed based on a frame of three-primary color image-pixel signals, which is composed of a frame of red image-pixel signals, a frame of green image-pixel signals, and a frame of blue image-pixel signals. In the simulated dye-spraying process, for example, a value of a central red image-pixel signal is compared with an average of values of eight circumferential red image-pixel signals surrounding the central red image-pixel signals.

If the value of the central signal is lower than the average of the values of the circumferential signals, the central red image-pixel signal derives from a fine recess area on a mucous membrane surface of, for example, a stomach. However, if the value of the central signal is higher than the average of the values of the circumferential signals, the central red image-pixel signal derives from a fine land area on the mucous membrane surface of the stomach. The same is true for the green image-pixel signals and the blue image-pixel signals.

Accordingly, for example, if the frame of three-primary color image-pixel signals is processed such that the values of red and green image-pixel signals, deriving from the fine recess areas, are lowered, an endoscope image can be reproduced as if it were sprayed with a bluish-solution.

Further, before the simulated dye-spraying process can be properly performed, it is necessary to take account of a spatial frequency of an endoscope image captured by the image sensor. Nevertheless, the aforesaid KOKAI No. 2001-25025 does not refer to the spatial frequency of the endoscope image captured by the image sensor.

In particular, when an unevenness on the mucous membrane surface of the stomach is captured by the image sensor, the captured unevenness image exhibits a specific spatial frequency. On the other hand, an image sensor has a specific pixel pitch, which is defined as an array pitch of photodiodes arranged on the light-receiving surface of the image sensor. In this case, for example, when the spatial frequency of the captured unevenness image is too low in comparison with the pixel pitch of the image sensor, it is impossible to properly perform the simulated dye-spraying process, because the eight circumferential image-pixels, surrounding the central image-pixel, do not necessarily represent a land area surrounding the fine recess represented by the central image-pixel signal.

For example, when an endoscope image to be reproduced on the TV monitor is enlarged, the spatial frequency of the enlarged endoscope image becomes lower than that of the original endoscope image, resulting in degraded performance of the simulated dye-spraying process. Also, when the video scope is substituted for another type of video scope featuring a solid-state image sensor having a smaller pixel pitch, the simulated dye-spraying process cannot be properly performed, because the spatial frequency of the endoscope image captured by the other type of video scope becomes relatively lower, due to the smaller pixel pitch of the image sensor thereof.

SUMMARY OF THE INVENTION

Therefore, an object of the present invention is to provide an electronic endoscope system with a color-balance alteration process, in which the color-balance alteration process can be properly performed regardless of the variation of spatial frequency of an endoscope image captured by a solid-state image sensor.

In accordance with the present invention, an electronic endoscope system includes a video scope having a solid-state image sensor that successively produces a frame of color image-pixel signals, and an image-signal processor that produces a color video signal based on the frame of color image-pixel signals. In this electronic endoscope system, a calculation system calculates a difference value between a value of a central single-color image-pixel signal and an average of values of some circumferential single-color image-pixel signals selected from single-color image-pixel signals surrounding the central single-color image-pixel signal. A color-balance alteration system alters the value of the central single-color image-pixel signal based on the difference value calculated by the calculation system. A selection system performs the selection of the circumferential single-color image-pixel signals such that the circumferential single-color image-pixel signals to be selected are farther from the central single-color image-pixel signal, as a spatial frequency of an endoscope image to be reproduced based on the color video signal is lower.

The calculation system may further include a multiplier system that multiplies the difference value by a density factor. In this case, the alteration of the value of the central single-color image-pixel signal by the color-balance alteration system is performed based on the multiplied difference value.

Preferably, the color-balance alteration system may further include a determination system that determines whether the value of the central single-color image-pixel signal is lower than the average of values, a subtraction system that subtracts the absolute value of the difference value from the value of the central single-color image-pixel signal when it is determined by the determination system that the value of the central single-color image-pixel signal is lower than the average of values, with the value of the central single-color image-pixel signal being unchanged when it is determined by the determination system that the value of the central single-color image-pixel signal is equal to or higher than the average of values.

In this case, the color-balance alteration system may be provided with a multiplier system that multiplies the difference value by a factor, and the absolute value of the multiplied difference value is subtracted from the value of the central single-color image-pixel signal by the subtraction system.

The selection system may be associated with an electronic zooming system introduced in the image-signal processor. Also, the selection system may be associated with an optical zooming system introduced in the video scope. Further, the selection system may be associated with a diaphragm system which maintains a constant overall luminance of the reproduced endoscope image. Furthermore, the selection system may be associated with at least two video scopes featuring different types of solid-state image sensors, which produce different numbers of image-pixel signals in one frame.

BRIEF DESCRIPTION OF THE DRAWINGS

The object and other objects of the present invention will be better understood from the following description, referring to the accompanying drawings, in which:

FIG. 5 is a conceptual view showing forty nine digital image-pixel signals in a 7×7 matrix, produced in the difference-calculation circuit shown in FIG. 4;

FIG. 7 is a table showing ten settings of values to be given to factors contained in the ten multipliers when selecting any one of the first to eighth factor-setting modes;

FIG. 8 is a table showing a factor-setting mode to be selected in accordance with the type of video scope being used at any one selected from magnifying powers of 1, 2, 3, and 4;

FIG. 27 is a table showing a factor-setting mode to be selected in accordance with the type of video scope used and a magnifying power attained by operating an optical zooming system introduced in the video scope;

FIG. 30 is a table showing a factor-setting mode to be selected in accordance with the type of video scope used and an opening value of a diaphragm;

DESCRIPTION OF THE PREFERRED EMBODIMENTS

Figure 1:
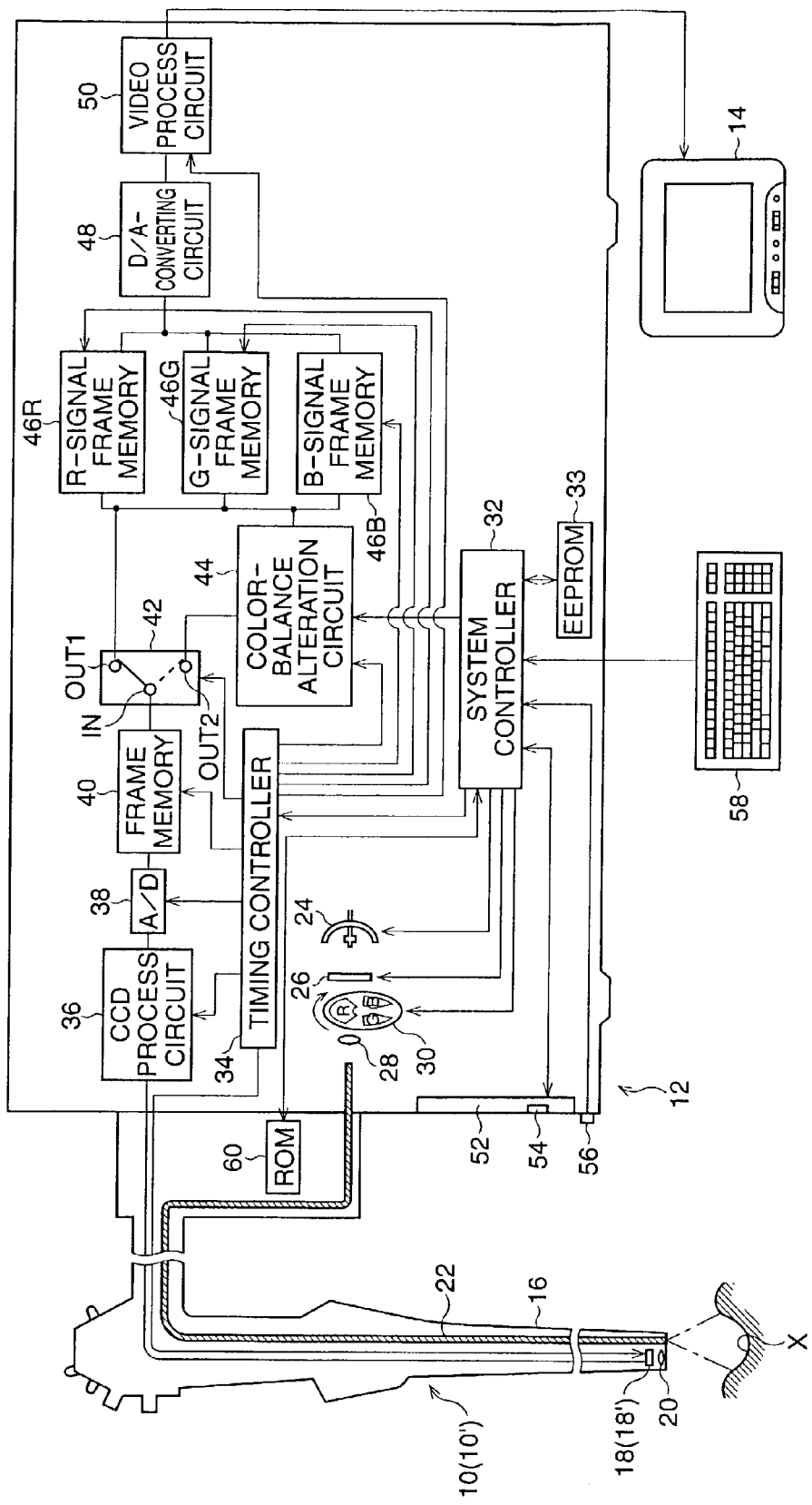
FIG. 1 is a schematic block diagram of a first embodiment of an electronic endoscope system according to the invention.

Referring to FIG. 1, a first embodiment of an electronic endoscope system according to the present invention is shown as a block diagram. The electronic endoscope system comprises a video scope 10, an image-signal processing unit 12 to which the video scope 10 is detachably coupled, and a TV monitor 14 to which the image-signal processing unit 12 is connected.

The video scope 10 is representative of various types of scopes, used for bronchial, esophageal, gastro, colon, etc. medical examinations. Namely, at least two different types of video scopes use the image-signal-processing unit 12 in common. This is because the scope 10 is detachably coupled to the image-signal processing unit 12.

The video scope 10 includes a flexible conduit 16 which is provided with a solid-state image sensor 18, such as a CCD (charge-coupled-device) image sensor, at the distal end thereof, and the CCD image sensor 18 is associated with an objective lens 20. When the connection is established between the video scope 10 and the image-signal processing unit 12, the CCD image sensor 18 is electrically connected to an image-signal processor provided in the image-signal processing unit 12.

Also, the video scope 10 includes a flexible optical light guide 22 extending therethrough and formed as a bundle of optical fibers. The optical light guide 22 terminates with a light-radiating end face at the distal end of the flexible conduit 16, and is associated with a lighting lens system (not shown) provided thereat. When the connection is established between the video scope 10 and the image-signal processing unit 12, the proximal end of the optical light guide 22 is optically connected to a light source device provided in the image-signal processing unit 12, whereby the light, emitted from the light source device, radiates as an illuminating-light from the light-radiating end face of the optical light guide 22.

When the flexible conduit 16 of the video scope 10 is inserted in an organ of a patient, an illuminated object is focused as an optical endoscope image on a light-receiving surface of the CCD image sensor 18, by the objective lens system 20 associated therewith. The focused endoscope image is converted into a frame of analog image-pixel signals by the CCD image sensor 18, and the frame of analog image-pixel signals is sequentially read from the image-signal processor provided in the image-signal processing unit 12, and a video signal is produced based on the read analog image-pixel signals, as discussed in detail hereinafter. Then, the video signal is fed from the image-signal processor to the TV monitor 14, and the endoscope image, sensed by the CCD image sensor 18, is reproduced as a motion picture on the TV monitor 14.

The light source device, provided in the image-signal processing unit 12, includes a white light lamp 24, such as a halogen lamp, a xenon lamp or the like, aligned with the proximal end of the light guide 22, a diaphragm 26 provided for regulating an amount of light directed from the lamp 24 to the proximal end of the light guide 22, and a condenser lens 28 provided for focusing the light on the proximal end of the light guide 22.

In this embodiment, in order to reproduce an endoscope image as a full color motion picture on the TV monitor 14, an RGB field sequential-type color imaging method is used in the electronic endoscope system. To this end, the light source device further includes a rotary color filter 30 provided between the diaphragm 26 and the condenser lens 28, and the rotary color filter comprises a disk element having three sector-shaped red, green, and blue filters. These filters are circumferentially and uniformly arranged such that three centers of the color filters are spaced from each other at regular angular intervals of 120 degrees, and a sector area between two adjacent color filters serves as a light-shielding area.

The rotary color filter 30 is rotated at a given rotational frequency in accordance with a commonly used image-reproduction method, such as the NTSC method, the PAL method and so on. For example, in the NTSC method, the rotational frequency of the rotary color-filter 30 is 30 Hz, and, in the PAL method, the rotational frequency of the rotary color-filter 30 is 25 Hz.

Thus, during the rotation of the rotary color filter 30, red, green and blue lights are cyclically and sequentially made incident on the proximal end of the light guide 22, whereby the red, green and blue lights are cyclically and sequentially emitted from the distal end face of the light guide 22. Namely, red, green, and blue endoscope images are sequentially and cyclically focused on the light-receiving surface of the CCD image sensor 18.

While the red, green, and blue endoscope images are cyclically focused on the light-receiving surface of the CCD image sensor 18 by the objective lens system 20, each of the red, green, and blue optical images is converted into a frame of monochromatic (red, green, blue) analog image-pixel signals by the CCD image sensor 18, and each frame of monochromatic analog image-pixel signals is read from the CCD image sensor 18 over a consecutive light-shielding time period which corresponds to the light-shielding area between two adjacent color filters of the rotary color filter 30.

As shown in FIG. 1, the image-signal processing unit 12 is provided with a system controller 32 which controls the electronic endoscope system as a whole. The system controller 32 contains a microcomputer comprising a central processing unit (CPU), a read-only memory (ROM) for storing programs and constants, a random-access memory (RAM) for storing temporary data, and an input/output interface circuit (I/O). The system controller 32 is also provided with a non-volatile memory 33, such as an electrically erasable programmable read-only memory (EEPROM) for storing and keeping various data. The image-signal processing unit 12 is also provided with a timing controller 34, which outputs various series of clock pulses having given frequencies under the control of the system controller 32, thereby operating sequentially and systematically the aforesaid image-signal processor provided in the image-signal processing unit 12.

Note, as is apparent from FIG. 1, the turn-ON and turn-OFF of the lamp 24, the operation of the diaphragm 26, and the rotation of the rotary color filter 30 are controlled by the system controller 32.

The image-signal processor, provided in the image-signal processing unit 12, includes a CCD process circuit 36. As shown in FIG. 1, when the connection is established between the video scope 10 and the image-signal processing unit 12, the CCD image sensor 18 is connected to the timing controller 34 and the CCD process circuit 36. The timing controller 34 produces and outputs a series of reading clock pulses to the CCD image sensor 18, whereby the three frames of monochromatic (red, green, and blue) analog image-pixel signals are cyclically and sequentially read from the CCD image sensor 18. The read analog image-pixel signals are fed to the CCD process circuit 36, in which the analog image-pixel signals are subjected to various image-processings, such as gamma-correction, white-balance correction, profile-enhancing, noise-elimination, black-level-clamping and so on. For these various image-processings, the CCD process circuit 36 is operated in accordance with various series of clock pulses output from the timing controller 34.

The image-signal processor further includes an analog-to-digital (A/D) converter 38, a frame memory 40, a switching-circuit 42, a simulated dye-spraying circuit or color-balance alteration circuit 44, a red-signal frame memory 46R, a green-signal frame memory 46G, a blue-signal frame memory 46B, a digital-to-analog (D/A) converting circuit 48, and a video process circuit 50.

Each of the processed analog image-pixel signals is output from the CCD process circuit 36 to the A/D converter 38, in which the analog image-pixel signal concerned is converted into a digital image-pixel signal. The conversion of the analog image-pixel signal into the digital image-pixel signal is performed in accordance with a series of sampling clock pulses output from the timing controller 34. Then, the digital image-pixel signal is temporarily stored in the frame memory 40. Namely, a frame of red digital image-pixel signals, a frame of green digital image-pixel signal, and a frame of blue image-pixel signals are cyclically and temporarily stored in the frame memory 40 in accordance with a series of writing clock pulses output from the timing controller 34. While the digital image-pixel signals are successively stored in the frame memory 40, the digital image-pixel signals are read from the frame memory 40 in order in accordance with a series of reading clock pulses output from the timing controller 34 to the frame memory 40.

Figure 2:
FIG. 2 is a conceptual view showing a frame of red digital image-pixel signals stored in an m×n matrix manner in a frame memory used in the first embodiment of the electronic endoscope system.

FIG. 2 conceptually shows, by way of example, a frame of red digital image-pixel signals $R_{11}$, $R_{12}$, ... $R_{m(n-1)}$, and $R_{mn}$, which are stored in a m×n matrix manner in the frame memory 40. Namely, a red image is formed by m horizontal-lines, each of which includes n digital image-pixel signals. The red digital image-pixel signals $R_{11}$, $R_{12}$, ... $R_{m(n-1)}$, and $R_{mn}$ are read from the frame memory 40 in a line-reading direction and in a pixel-reading direction indicated by arrows in FIG. 2, and are then fed to the switching-circuit 42. In this embodiment, each of the digital image-pixel signals $R_{11}$, $R_{12}$, ... $R_{m(n-1)}$, and $R_{mn}$ is composed of eight bits, and represents any one of 256 level values. The same is true for the green digital image-pixel signals $G_{11}$, $G_{12}$, ... $G_{m(n-1)}$, and $G_{mn}$, and the blue digital image-pixel signals $B_{11}$, $B_{12}$, ... $B_{m(n-1)}$, and $B_{mn}$.

Note, the storage of the digital image-pixel signals in the frame memory 40 is performed in accordance with a series of writing-clock pulses output from the timing controller 34, and the reading of the digital image-pixel signals from the frame memory 40 is performed in accordance with a series of reading-clock pulses.

The switching-circuit 42 has an input terminal "IN", a first output terminal "OUT1", and a second output terminal "OUT2". The switching of the connection of the input terminal "IN" from the first output terminal "OUT1" to the second output terminal "OUT2" and vice versa is performed by a switching pulse output from the timing controller 34.

In this embodiment, either a usual display mode or a simulated dye-spraying display mode is selected. When the usual display mode is selected, the input terminal "IN" is connected to the first output terminal "OUT1", such that the digital image-pixel signal, read from the frame memory 40, is directly output from the first output terminal "OUT1" to any one of the red-signal, green-signal, and blue-signal frame memories 46R, 46G, and 46B. Namely, when the digital image-pixel signal is red, it is stored in the red-signal frame memory 46R; when the digital image-pixel signal is green, it is stored in the green-signal frame memory 46G; and when the digital image-pixel signal is blue, it is stored in the blue-signal frame memory 46B.

When the simulated dye-spraying display mode is selected, the connection of the input terminal "IN" is switched between the first output terminal "OUT1" and the second output terminal "OUT2", such that the respective frames of red and green image-pixel signals are fed from the frame memory 40 to the red-signal and green-signal frame memories 46R and 46G through the color-balance alteration circuit 44, and such that the frame of blue image-pixel signals is directly fed to and stored in the blue-signal frame memory 46B. Namely, only the frames of red and green image-pixel signals are subjected to a color-balance alteration process in the color-balance alteration circuit 44. The processed red and green image-pixel signals are respectively fed to and stored in the red-signal and green-signal frame memories 46R and 46G.

Note, the storage of the digital image-pixel signals in each frame memory (46R, 46G, 46) is performed in accordance with a series of writing clock pulses output from the timing controller 34.

The red, green, and blue digital image-pixel signals are simultaneously read from the red-signal, green-signal, and blue-signal frame memories 46R, 46G, and 46, and are then output to the D/A converting circuit 48. The D/A converting circuit 48 includes three digital-to-analog (D/A) converters, and the respective red, green, and blue digital image-pixel signals are simultaneously converted into red, green, and blue analog image signals by the three D/A converters.

Then, the red, green, and blue analog image signals are output from the D/A converting circuit 48 to the video process circuit 50. On the other hand, the timing controller 34 produces a composite synchronizing signal, and the composite synchronizing signal is output from the timing controller 34 to the video process circuit 50. Thus, the video process circuit 50 produces a component type video signal based on the red, green, and blue image signals output from the D/A converting circuit 48 and the composite synchronizing signal output from the timing controller 34.

In the video process circuit 50, the component type video signal is also subjected to suitable image-processings, such as high frequency noise-elimination, profile-enhancing, and so on. Then, the processed component type video signal is fed from the video process circuit 50 to the TV video monitor 14. Thus, optical endoscope images, successively captured by the CCD image sensor 18, are reproduced as a full color motion picture on the TV monitor 14.

While the usual display mode is selected, the endoscope image is reproduced on the TV monitor with a given proper color balance. However, while the simulated dye-spraying display mode is selected, the endoscope image is reproduced on the TV monitor 14 as if it were sprayed with a blue-solution, due to the color-balance alteration process of the red and green digital image-pixel signals in the color-balance alteration circuit 44, as stated in detail hereinafter.

Note, the video process circuit 50 may include a color encoder for producing various video signals, a S-video signal, a composite type video signal and so on, based on the component type video signal.

In FIG. 1, reference 52 indicates a front panel attached to a front wall of a housing of the image-signal processing unit 12, and reference 54 indicates a display-mode selection switch 54 provided on the front panel 52. Also, reference 56 indicates a power ON/OFF switch provided on the front wall of the housing of the image-signal processing unit 12.

The display-mode selection switch 54 is provided for selecting either the usual display mode or the simulated dye-spraying display mode. The display-mode selection switch 54 is constituted to alternately output a high-level signal or a low-level signal to the system controller 32 whenever it is operated. When the high-level signal is output from the display-mode selection switch 54, the system controller 32 recognizes that the simulated dye-spraying display mode is selected. When the low-level signal is output from the display-mode selection switch 54, the system controller 32 recognizes that the usual display mode is selected. In short, whenever the display-mode selection switch 54 is operated, the usual display mode and the simulated dye-spraying display mode are alternately selected.

When the power ON/OFF switch 56 is turned ON, the image-signal processing unit 12 is supplied with electric power from a commercial power source. Note, when the power ON/OFF switch 56 is turned ON, the low-level signal is output from the display-mode selection switch 54, and the usual display mode is forcibly selected.

As shown in FIG. 1, a keyboard 58 is connected to the system controller 32 of the image-signal processing unit 12 to input various commands and various data to the system controller 32. A function, pertaining to the display-mode selection switch 54, may be allocated to a function key on the keyboard 58. When the display-mode selection is performed by the function key on the keyboard 58, the display-mode selection switch 54 may be eliminated from the front panel 52.

In this embodiment, it is intended that another type of video scope 10', having a CCD image sensor 18', is substituted for the video scope 10. Note, in FIG. 1, respective references 10' and 18' are put in brackets adjacent to references 10 and 18.

As is apparent from the foregoing, the CCD image sensor 18 of the video scope 10 is constituted so as to produce a frame of m×n image-pixel signals. On the other hand, the CCD image sensor 18' of the video scope 10' is constituted so as to produce a frame of M×N image-pixel signals which is more than the number of m×n image-pixel signals (M>m, N>n). In this case, the CCD image sensor 18 of the video scope 10 features a larger pixel pitch than that of the CCD image sensor 18' of the video scope 10'.

The frame of M×N image-pixel signals, obtained from the CCD image sensor 18', must be processed in the image-signal processor at a timing that is different from the timing at which the frame of m×n image-pixel signals are processed, before an endoscope image, based on the number of M×N image-pixel signals, can be properly reproduced on the TV monitor 14. Thus, the system controller 32 must recognize what type of video scope is connected to the image-signal processing unit 12.

To this end, the video scope (10, 10') is provided with a read-only memory (ROM) 60 for storing pixel-number data, which represent either the number of m×n image-pixel signals or the number of M×N image-pixel signals. When a connection is established between the video scope (10, 10') and the image-signal processing unit 12, the ROM 60 is connected to the system controller 32, as shown in FIG. 1, whereby the pixel-number data is retrieved from the ROM 60 by the system controller 32. Thus, the system controller 32 can recognize what type of video scope (10, 10') is used. As stated above, since the timing controller 34 is operated under the control of the system controller 32, it is possible for the timing controller 34 to produce and output various series of clock pulses having given frequencies based on the pixel number data, such that either of the frame of m×n image-pixel signals or the frame of M×N image-pixel signals can be processed in the image-signal processor at a proper timing.

In the first embodiment, an electronic zooming system is introduced into the image-signal processor, provided in the image-signal processing unit 12, and thus it is possible to reproduce an endoscope image on the TV monitor 14 at any one of the magnifying powers of 1, 2, 3, and 4, using the electronic zooming system.

In particular, when the image-signal processing unit 12 is electrically powered ON by the power ON/OFF switch 56, a one-power display mode is forcibly selected. Namely, usually, the endoscope image is reproduced on the TV monitor 14 at the magnifying power of 1.

When a two-power display mode is selected, the frequency of the sampling clock pulses output from the timing controller 34 to the A/D converter 38 is increased two times, and the frequency of the writing clock pulses output from the timing controller 34 to the frame memory 40 is also increased two times. However, the frequency of the reading clock pulses output from the timing controller 34 to the frame memory 40 is unchanged. Thus, the reproduced endoscope image on the TV monitor 14 is enlarged by the magnifying power of 2.

Also, when a three-power display mode is selected, the frequency of the sampling clock pulses output from the timing controller 34 to the A/D converter 38 is increased three times, and the frequency of the writing clock pulses output from the timing controller 34 to the frame memory 40 is also increased three times. However, the frequency of the reading clock pulses output from the timing controller 34 to the frame memory 40 is unchanged. Thus, the reproduced endoscope image on the TV monitor 14 is enlarged by the magnifying power of 3.

Further, when a four-power display mode is selected, the frequency of the sampling clock pulses output from the timing controller 34 to the A/D converter 38 is increased four times, and the frequency of the writing clock pulses output from the timing controller 34 to the frame memory 40 is also increased four times. However, the frequency of the reading clock pulses output from the timing controller 34 to the frame memory 40 is unchanged. Thus, the reproduced endoscope image on the TV monitor 14 is enlarged by the magnifying power of 4.

As discussed hereinbefore, it is necessary to take account of a spatial frequency of an endoscope image captured by the CCD image sensor (18, 18') before the color-balance alteration process can be properly performed. Accordingly, for example, when a magnifying-power display mode is changed to another magnifying-power display mode and/or when the video scope 10, featuring the m×n image-pixel signals, is substituted for the video scope 10' featuring the M×N image-pixel signals, the color-balance alteration process must be modified in accordance with the substitution of the different type of video scope and/or the change of the magnifying-power display mode. This is because the spatial frequency of the captured endoscope image varies due to the substitution of the different type of video scope and/or the change of the magnifying-power display mode.

In the first embodiment, the color-balance alteration process circuit 44 is constituted so as to cope with the substitution of the different type of video scope and/or the change of the magnifying-power display mode.

Figure 3:
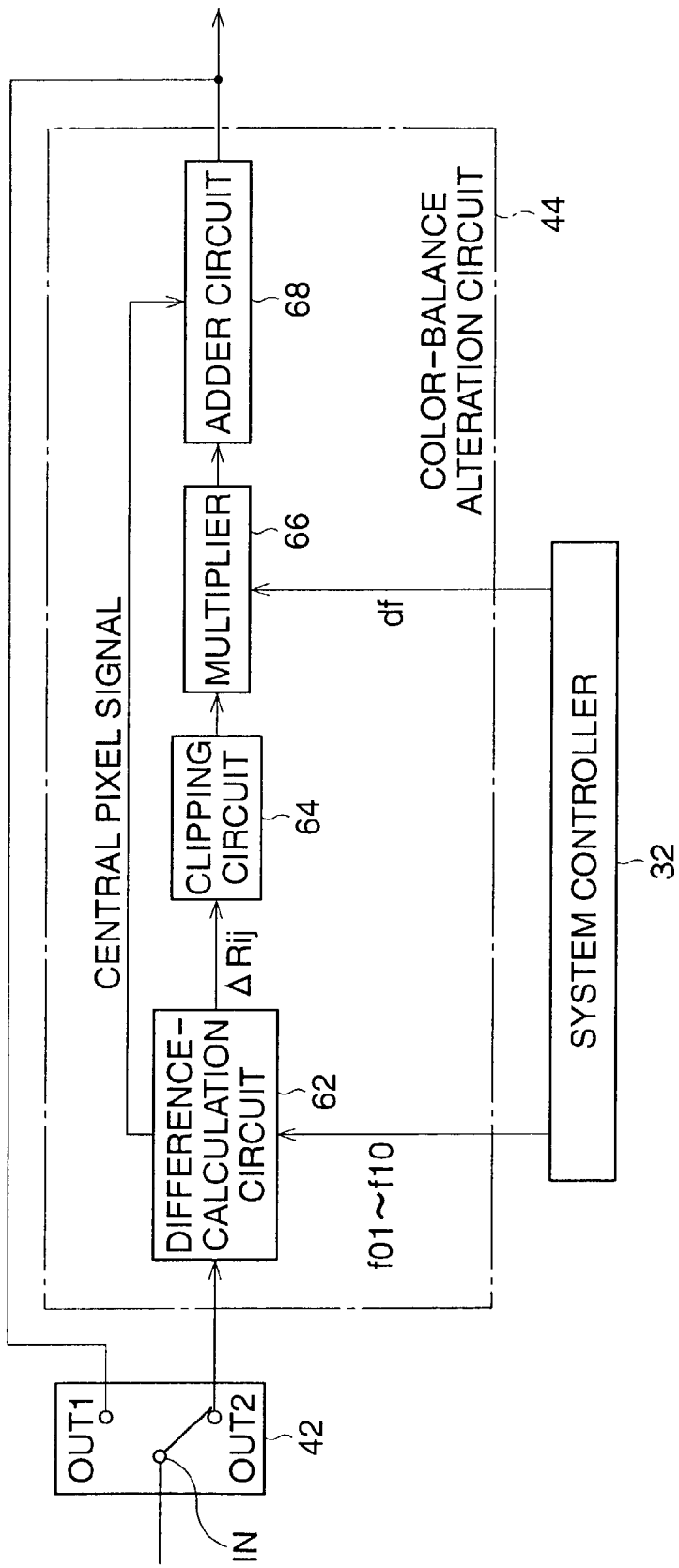
FIG. 3 is a schematic block diagram of a color-balance alteration circuit used in the first embodiment of the electronic endoscope system.
Figure 4:
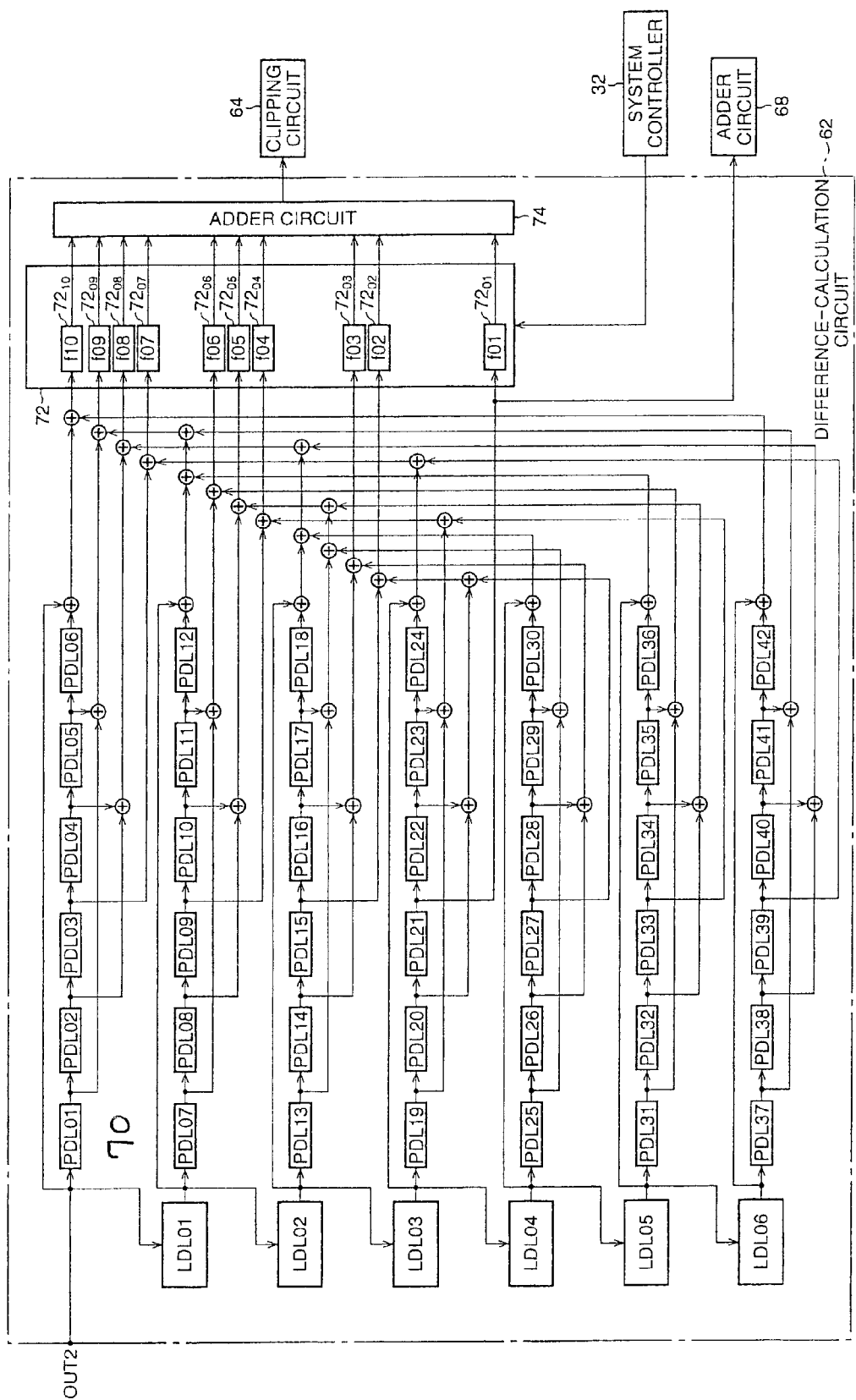
FIG. 4 is a schematic block diagram of a difference-calculation circuit included in the color-balance alteration circuit shown in FIG. 3.

As shown in FIG. 3, the color-balance alteration circuit 44 comprises a difference-calculation circuit 62, a clipping circuit 64, a multiplier 66, and an adder 68. Also, as shown in FIG. 4, the difference calculation circuit 62 includes a delay circuit arrangement 70 comprising six one-line delay circuits LDL01, ... , and LDL06, and forty two one-pixel delay circuits PDL01, ... , and PDL42. The difference-calculation circuit 62 also includes thirty nine adders, symbolically shown in FIG. 4, and these adders are associated with the delay circuit arrangement 70, as shown in FIG. 4. The difference-calculation circuit 62 further includes a multiplier circuit 72, and an adder circuit 74. The multiplier circuit 72 includes ten multipliers $72_{01}$, $72_{02}$, ... , $72_{09}$, and $72_{10}$, and factors f01, f02, ... , f09, and f10 are respectively set in the multipliers $72_{01}$, $72_{02}$, ... , $72_{09}$, and $72_{10}$.

Each of the one-line delay circuits LDL01 to LDL06 outputs an input digital image-pixel signal after the time necessary for reading one horizontal-line of digital image-pixel signals from the frame memory 40 has elapsed. Namely, the outputting of the digital image-pixel signal from each one-line delay circuit is delayed for the reading time of the one horizontal-line of digital image-pixel signals.

On the other hand, each of the one-pixel delay circuits PDL01 to PDL42 outputs an input digital image-pixel signal after the time necessary for reading one digital image-pixel signal from the frame memory 40 has elapsed. Namely, the outputting of the digital image-pixel signal from each one-pixel delay circuit is delayed for the reading time of the one digital image-pixel signal.

Thus, in the simulated dye-spraying display mode, for example, while the red digital image-pixel signals $R_{11}$, $R_{12}$, ... $R_{m(n-1)}$, and $R_{mn}$ are successively fed one by one from the frame memory 40 to the color-balance alteration circuit 44, a set of forty nine red digital image-pixel signals $R_{(i-3)(j-3)}$, $R_{(i-3)(j-2)}$, ... , $R_{ij}$, ... , $R_{(i+3)(j+2)}$, and $R_{(i+3)(j+3)}$ is produced in the delay circuit arrangement 70 ($4 \leq i \leq (m-3)$, and $4 \leq j \leq (n-3)$), and these red digital image-pixel signals form a 7×7 matrix, as shown in FIG. 5. As is apparent from this drawing, the pixel signal $R_{ij}$ forms a central pixel signal surrounded by the remaining forty-eight pixel signals $R_{(i-3)(j-3)}$, ... , $R_{i(j-1)}$, $R_{i(j+1)}$, ... , and $R_{(i+3)(j+3)}$.

When the pixel signal $R_{(i+3)(j+3)}$ is input to the delay circuit arrangement 70, the one-line delay circuits LDL01 to LDL06 respectively output the pixel signals $R_{(i+2)(j+3)}$, $R_{(i+1)(j+3)}$, ... , $R_{(i-2)(j+3)}$ and $R_{(i-3)(j+3)}$; the one-pixel delay circuits PDL01 to PDL06 respectively output the pixel signals $R_{(i+3)(j+2)}$, $R_{(i+3)(j+1)}$, ... , $R_{(i+3)(j-2)}$ and $R_{(i+3)(j-3)}$; the one-pixel delay circuits PDL07 to PDL12 respectively output the pixel signals $R_{(i+2)(j+2)}$, $R_{(i+2)(j+1)}$, ... , $R_{(i+2)(j-2)}$ and $R_{(i+2)(j-3)}$; the one-pixel delay circuits PDL13 to PDL18 respectively output the pixel signals $R_{(i+1)(j+2)}$, $R_{(i+1)(j+1)}$, ... , $R_{(i+1)(j-2)}$ and $R_{(i+1)(j-3)}$; the one-pixel delay circuits PDL19 to PDL24 respectively output the pixel signals $R_{i(j+2)}$, $R_{i(j+1)}$, ... , $R_{i(j-2)}$ and $R_{i(j-3)}$; the one-pixel delay circuits PDL25 to PDL30 respectively output the pixel signals $R_{(i-1)(j+2)}$, $R_{(i-1)(j+1)}$, ... , $R_{(i-1)(j-2)}$ and $R_{(i-1)(j-3)}$; the one-pixel delay circuits PDL31 to PDL36 respectively output the pixel signals $R_{(i-2)(j+2)}$, $R_{(i-2)(j+1)}$, ... , $R_{(i-2)(j-2)}$ and $R_{(i-2)(j-3)}$; and the one-pixel delay circuits PDL37 to PDL42 respectively output the pixel signals $R_{(i-3)(j+2)}$, $R_{(i-3)(j+1)}$, ... , $R_{(i-3)(j-2)}$ and $R_{(i-3)(j-3)}$.

Figure 6:
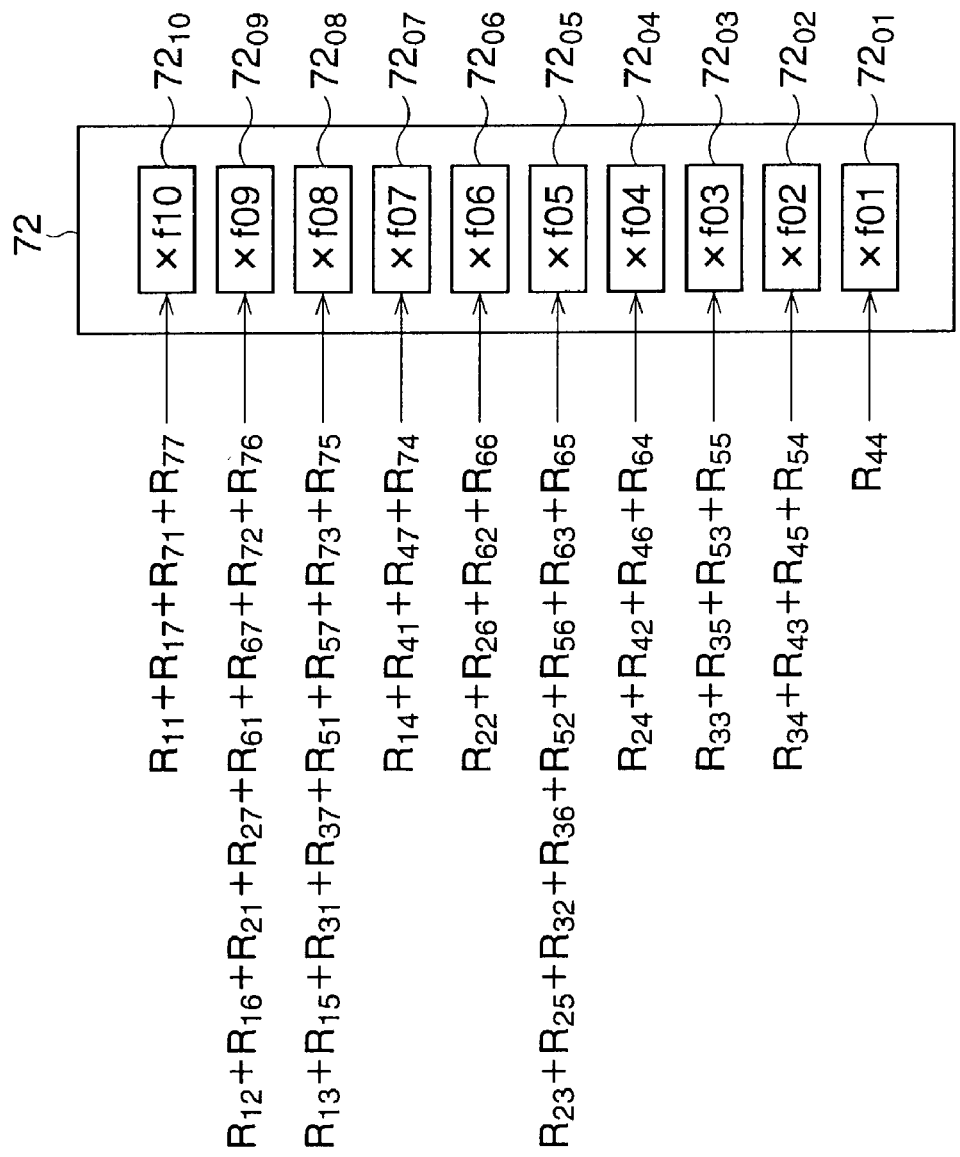
FIG. 6 is a conceptual view showing relationships between ten multipliers of a multiplier circuit included in the difference-calculation circuit and the forty nine image-pixel signals to be input thereto.

As is apparent from FIG. 4, the central pixel signal $R_{ij}$ is output from the one-pixel delay circuit PDL21, and is then input to the first multiplier $72_{01}$. For example, when the pixel signal $R_{77}$ is input to the color-balance alteration circuit 44, the pixel signal $R_{44}$ is input as a central pixel signal from the one-pixel delay circuit PDL21 to the first multiplier $72_{01}$, as shown in FIG. 6.

On the other hand, each of the forty-eight circumferential pixel signals $R_{(i-3)(j-3)}$, ... , $R_{i(j-1)}$, $R_{i(j+1)}$, ... , and $R_{(i+3)(j+3)}$ is input to any one of the multipliers $72_{02}$ to $72_{10}$ in accordance with the arrangement of the thirty nine adders (symbolically shown in FIG. 4) associated with the delay circuit arrangement 70, as stated below.

The values of the pixel signals $R_{(i-1)j}$, $R_{i(j-1)}$, $R_{i(j+1)}$, and $R_{(i+1)j}$ are summed, and are then input to the second multiplier $72_{02}$. As is apparent from FIG. 5, the pixel signals $R_{(i-1)j}$, $R_{i(j-1)}$, $R_{i(j+1)}$, and $R_{(i+1)j}$ are equally spaced from the central pixel signal $R_{ij}$ by a distance of "d", which corresponds to the pixel pitch of the photodiodes arranged on the light-receiving surface of the CCD image sensor 18 in the m×n matrix manner. For example, when the pixel signal $R_{77}$ is input to the color-balance alteration circuit 44, the sum of the values of the pixel signals $R_{34}$, $R_{43}$, $R_{45}$, and $R_{54}$ is input to the second multiplier $72_{02}$, as shown in FIG. 6.

The values of the pixel signals $R_{(i-1)(j-1)}$, $R_{(i-1)(j+1)}$, $R_{(i+1)(j-1)}$, and $R_{(i+1)(j+1)}$ are summed, and are then input to the third multiplier $72_{03}$. As is apparent from FIG. 5, the pixel signals $R_{(i-1)(j-1)}$, $R_{(i-1)(j+1)}$, $R_{(i+1)(j-1)}$, and $R_{(i+1)(j+1)}$ are equally spaced from the central pixel signal $R_{ij}$ by a distance of approximately "1.41*d" calculated based on the Pythagorean theorem. For example, when the pixel signal $R_{77}$ is input to the color-balance alteration circuit 44, the sum of the values of the pixel signals $R_{33}$, $R_{35}$, $R_{53}$, and $R_{55}$ is input to the third multiplier $72_{03}$, as shown in FIG. 6.

The values of the pixel signals $R_{(i-2)j}$, $R_{i(j-2)}$, $R_{i(j+2)}$, and $R_{(i+2)j}$ are summed, and are then input to the fourth multiplier $72_{04}$. As is apparent from FIG. 5, the pixel signals $R_{(i-2)j}$, $R_{i(j-2)}$, $R_{i(j+2)}$, and $R_{(i+2)j}$ are equally spaced from the central pixel signal $R_{ij}$ by a distance of "2*d". For example, when the pixel signal $R_{77}$ is input to the color-balance alteration circuit 44, the sum of the values of the pixel signals $R_{24}$, $R_{42}$, $R_{46}$, and $R_{64}$ is input to the forth multiplier $72_{04}$, as shown in FIG. 6.

The values of the pixel signals $R_{(i-2)(j-1)}$, $R_{(i-2)(j+1)}$, $R_{(i-1)(j-2)}$, $R_{(i-1)(j+2)}$, $R_{(i+1)(j-2)}$, $R_{(i+1)(j+2)}$, $R_{(i+2)(j-1)}$, and $R_{(i+2)(j+1)}$ are summed, and are then input to the fifth multiplier $72_{05}$. As is apparent from FIG. 5, the pixel signals $R_{(i-2)(j-1)}$, $R_{(i-2)(j+1)}$, $R_{(i-1)(j-2)}$, $R_{(i-1)(j+2)}$, $R_{(i+1)(j-2)}$, $R_{(i+1)(j+2)}$, $R_{(i+2)(j-1)}$, and $R_{(i+2)(j+1)}$ are equally spaced from the central pixel signal $R_{ij}$ by a distance of approximately "2.24*d". For example, when the pixel signal $R_{77}$ is input to the color-balance alteration circuit 44, the sum of the values of the pixel signals $R_{23}$, $R_{25}$, $R_{32}$, $R_{36}$, $R_{52}$, $R_{56}$, $R_{63}$, and $R_{65}$ is input to the fifth multiplier $72_{05}$, as shown in FIG. 6.

The values of the pixel signals $R_{(i-2)(j-2)}$, $R_{(i-2)(j+2)}$, $R_{(i+2)(j-2)}$, and $R_{(i+2)(j+2)}$ are summed, and are then input to the sixth multiplier $72_{06}$. As is apparent from FIG. 5, the pixel signals $R_{(i-2)(j-2)}$, $R_{(i-2)(j+2)}$, $R_{(i+2)(j-2)}$, and $R_{(i+2)(j+2)}$ are equally spaced from the central pixel signal $R_{ij}$ by a distance of approximately "2.83*d". For example, when the pixel signal $R_{77}$ is input to the color-balance alteration circuit 44, the sum of the values of the pixel signals $R_{22}$, $R_{26}$, $R_{62}$, and $R_{66}$ is input to the sixth multiplier $72_{06}$, as shown in FIG. 6.

The values of the pixel signals $R_{(i-3)j}$, $R_{i(j-3)}$, $R_{i(j+3)}$, and $R_{(i+3)j}$ are summed, and are then input to the seventh multiplier $72_{07}$. As is apparent from FIG. 5, the pixel signals $R_{(i-3)j}$, $R_{i(j-3)}$, $R_{i(j+3)}$, and $R_{(i+3)j}$ are equally spaced from the central pixel signal $R_{ij}$ by a distance of "3*d". For example, when the pixel signal $R_{77}$ is input to the color-balance alteration circuit 44, the sum of the values of the pixel signals $R_{14}$, $R_{41}$, $R_{47}$, and $R_{74}$ is input to the seventh multiplier $72_{07}$, as shown in FIG. 6.

The values of the pixel signals $R_{(i-3)(j-1)}$, $R_{(i-3)(j+1)}$, $R_{(i-1)(j-3)}$, $R_{(i-1)(j+3)}$, $R_{(i+1)(j-3)}$, $R_{(i+1)(j+3)}$, $R_{(i+3)(j-1)}$, and $R_{(i+3)(j+1)}$ are summed, and are then input to the eighth multiplier $72_{08}$. As is apparent from FIG. 5, the pixel signals $R_{(i-3)(j-1)}$, $R_{(i-3)(j+1)}$, $R_{(i-1)(j-3)}$, $R_{(i-1)(j+3)}$, $R_{(i+1)(j-3)}$, $R_{(i+1)(j+3)}$, $R_{(i+3)(j-1)}$, and $R_{(i-3)(j+1)}$ are equally spaced from the central pixel signal $R_{ij}$ by a distance of approximately "3.16*d". For example, when the pixel signal $R_{77}$ is input to the color-balance alteration circuit 44, the sum of the values of the pixel signals $R_{13}$, $R_{15}$, $R_{31}$, $R_{37}$, $R_{51}$, $R_{57}$, $R_{73}$, and $R_{75}$ is input to the eighth multiplier $72_{08}$, as shown in FIG. 6.

The values of the pixel signals $R_{(i-3)(j-2)}$, $R_{(i-3)(j+2)}$, $R_{(i-2)(j-3)}$, $R_{(i-2)(j+3)}$, $R_{(i+2)(j-3)}$, $R_{(i+2)(j+3)}$, $R_{(i+3)(j-2)}$, and $R_{(i+3)(j+2)}$ are summed, and are then input to the ninth multiplier $72_{09}$. As is apparent from FIG. 5, the pixel signals $R_{(i-3)(j-2)}$, $R_{(i-3)(j+2)}$, $R_{(i-2)(j-3)}$, $R_{(i-2)(j+3)}$, $R_{(i+2)(j-3)}$, $R_{(i+2)(j+3)}$, $R_{(i+3)(j-2)}$, and $R_{(i+3)(j+2)}$ are equally spaced from the central pixel signal $R_{ij}$ by a distance of approximately "3.61*d". For example, when the pixel signal $R_{77}$ is input to the color-balance alteration circuit 44, the sum of the values of the pixel signals $R_{12}$, $R_{16}$, $R_{21}$, $R_{27}$, $R_{61}$, $R_{67}$, $R_{72}$, and $R_{76}$ is input to the ninth multiplier $72_{09}$, as shown in FIG. 6.

The values of the pixel signals $R_{(i-3)(j-3)}$, $R_{(i-3)(j+3)}$, $R_{(i+3)(j-3)}$, and $R_{(i+3)(j+3)}$ are summed, and are then input to the tenth multiplier $72_{10}$. As is apparent from FIG. 5, the pixel signals $R_{(i-3)(j-3)}$, $R_{(i-3)(j+3)}$, $R_{(i+3)(j-3)}$, and $R_{(i+3)(j+3)}$ are equally spaced from the central pixel signal $R_{ij}$ by a distance of approximately "4.24*d". For example, when the pixel signal $R_{77}$ is input to the color-balance alteration circuit 44, the sum of the values of the pixel signals $R_{11}$, $R_{17}$, $R_{71}$, and $R_{77}$ is input to the then multiplier $72_{10}$, as shown in FIG. 6.

The difference-calculation circuit 62 is used to calculate a difference $\Delta R_{ij}$ between a value of the central pixel signal $R_{ij}$ and an average value of some circumferential pixel signals selected from the forty-eight pixel signals except for the central pixel signal $R_{ij}$, and the selection of some circumferential pixel signals is performed in accordance with the variation of the spatial frequency of an endoscope image to be reproduced on the TV monitor 14.

Supposing that either the video scope 10, featuring the m×n pixels, or the video scope 10', featuring M×N pixels, is connected to the image-signal processing unit 12, when the video scope 10' (M×N) is utilized, and when the one-power display mode is selected, the reproduced endoscope image on the TV monitor 14 exhibits the highest spatial frequency. Also, when the video scope 10 (m×n) is utilized, and when the four-power display mode is selected, the reproduced endoscope image on the TV monitor 14 exhibits the lowest spatial frequency.

Thus, the calculation of the difference $\Delta R_{ij}$ is performed by the difference-calculation circuit 62, as stated below.

When the reproduced endoscope image on the TV monitor 14 exhibits the highest spatial frequency (i.e. when the video scope 10' (M×N) is utilized), and when the one-power display mode is selected), the respective settings of "1" and "−¼" are given to the factors f01 and f02, and a setting of "0" is given to all the remaining factors f03 to f10, in accordance with a first factor-setting mode (1st. MODE) of the "FACTOR-SETTING TABLE" shown in FIG. 7. Thus, the circumferential pixel signals $R_{(i-1)j}$, $R_{i(j-1)}$, $R_{i(j+1)}$, and $R_{(i+1)j}$, which are closest to the central pixel signal $R_{ij}$, are selected for the calculation of the difference $\Delta R_{ij}$. For example, when the central pixel signal $R_{ij}$ is $R_{44}$, in the adder circuit 74, the following calculation is performed:

$$\Delta R_{44} = [R_{44} - (R_{34} + R_{43} + R_{45} + R_{54})/4]$$

Also, when the reproduced endoscope image on the TV monitor 14 exhibits the lowest spatial frequency (i.e. when the video scope 10 (m×n) is utilized), and when the four-power display mode is selected, the respective settings of "1" and "−¼" are given to the factors f01 and f10, and a setting of "0" is given to all the remaining factors f02 to f09, in accordance with an eighth factor-setting mode (8th. MODE) of the "FACTOR-SETTING TABLE" shown in FIG. 7. Thus, the circumferential pixel signals $R_{(i-3)(j-3)}$, $R_{(i-3)i(j+3)}$, $R_{(i+3)(j-3)}$, and $R_{(i+3)(j+3)}$, which are farthest to the central pixel signal $R_{ij}$, are selected for the calculation of the difference $\Delta R_{ij}$. For example, when the central pixel signal $R_{ij}$ is $R_{44}$, in the adder circuit 74, the following calculation is performed:

$$\Delta R_{44} = [R_{44} - (R_{11} + R_{17} + R_{71} + R_{77})/4]$$

Namely, when the video scope 10' (M×N) is utilized, any one of the first, third, fifth, and seventh factor-setting modes is selected from the "FACTOR-SETTING TABLE" of FIG. 7 in accordance with the selection of the magnifying powers of "1", "2", "3", and "4", as shown in the "FACTOR-SETTING-MODE SELECTION TABLE" of FIG. 8. Similarly, when the video scope 10 (m×n) is utilized, any one of the second, fourth, sixth, and eighth factor-setting modes is selected from the "FACTOR-SETTING TABLE" of FIG. 7 in accordance with the selection of the magnifying powers of "1", "2", "3", and "4", as shown in the "FACTOR-SETTING-MODE SELECTION TABLE" of FIG. 8.

For example, when the video scope 10' (M×N) is utilized, and when the two-power display mode is selected, the respective settings of "1", "−⅛", and "−⅛" are given to the factors f01, f03, and f04, and a setting of "0" is given to all the remaining factors f02, f05 to f10, in accordance with the third factor-setting mode (3rd. MODE) of the "FACTOR-SETTING TABLE" shown in FIG. 7. Thus, the circumferential pixel signals $R_{(i-1)(j-1)}$, $R_{(i-1)(j+1)}$, $R_{(i+1)(j-1)}$, $R_{(i+1)(j+1)}$, $R_{(i-2)j}$, $R_{i(j-2)}$, $R_{i(j+2)}$, and $R_{(i+2)j}$ are selected for the calculation of the difference $\Delta R_{ij}$. Accordingly, for example, if $R_{ij} = R_{44}$, in the adder circuit 74, the following calculation is performed:

$$\Delta R_{44} = [R_{44} - (R_{33} + R_{35} + R_{53} + R_{55} + R_{24} + R_{42} + R_{46} + R_{64})/8]$$

Also, for example, when the video scope 10 (m×n) is utilized, and when the two-power display mode is selected, the respective settings of "1", "−1/12", and "−1/12" are given to the factors f01, f04, and f05, and a setting of "0" is given to all the remaining factors f02, f03, f06 to f10, in accordance with the fourth factor-setting mode (4th. MODE) of the "FACTOR-SETTING TABLE" shown in FIG. 7. Thus, the circumferential pixel signals $R_{(i-2)j}$, $R_{i(j-2)}$, $R_{i(j+2)}$, $R_{(i+2)j}$, $R_{(i-2)(j-1)}$, $R_{(i-2)(j+1)}$, $R_{(i-1)(j-2)}$, $R_{(i-1)(j+2)}$, $R_{(i+1)(j-2)}$, $R_{(i+1)(j+2)}$, $R_{(i+2)(j-1)}$, and $R_{(i+2)(j+1)}$ are selected for the calculation of the difference $\Delta R_{ij}$. Accordingly, for example, if $R_{ij}=R_{44}$, in the adder circuit 74, the following calculation is performed:

$$\Delta R_{44}=[R_{44}-(R_{24}+R_{42}+R_{46}+R_{64}+R_{23}+R_{25}+R_{32}$$
$$R_{36}+R_{52}+R_{56}+R_{63}R_{65})/12)]$$

Of course, when the green digital image-pixel signals $G_{11}$, $G_{12}$, ... $G_{m(n-1)}$, and $G_{mn}$ are fed from the frame memory 40 to the color-balance alteration circuit 44, the difference-calculation circuit 62 calculates a difference $\Delta G_{ij}$ between a value of a central digital image-pixel signal $G_{ij}$ and an average value of some circumferential pixel signals selected from the forty-eight signals $G_{(i-3)(j-3)}$, ..., $G_{i(j-1)}$, $G_{i(j+1)}$, ..., and $G_{(i+3)(j+3)}$ except for the central pixel signals $G_{ij}$, and the selection of some circumferential pixel signals is performed in the same manner as mentioned above.

The difference or value ($\Delta R_{ij}$, $\Delta G_{ij}$) is output from the adder circuit 74 to the clipping circuit 64, in which a zero is set as a clipping level. Namely, when the value ($\Delta R_{ij}$, $\Delta G_{ij}$) is either zero or plus, it is output as a zero signal from the clipping circuit 64 to the multiplier 66. On the other hand, when the value ($\Delta R_{ij}$, $\Delta G_{ij}$) is minus, it is output as a minus signal from the clipping circuit 64 to the multiplier 66. In short, only the minus value ($\Delta R_{ij}$, $\Delta G_{ij}$) included in a frame can pass through the clipping circuit 84 as they stand, and all the remaining value ($\Delta R_{ij}$, $\Delta G_{ij}$) included in a frame are output as the zero signal from the clipping circuit 64.

The multiplier 66 contains a density factor "df" set therein, and the density factor "df" is manually and stepwisely variable, as stated in detail hereinafter. At any event, the setting of a suitable plus value is given to the density factor "df" in the multiplier 66. The signal ($\Delta R_{ij}$, $\Delta G_{ij}$), output from the clipping circuit 64, is input to the multiplier 66, in which the signal ($\Delta R_{ij}$, $\Delta G_{ij}$) is multiplied by the density factor "df". Namely, the multiplier 66 outputs the products (df*$\Delta R_{ij}$, df*$\Delta G_{ij}$) as a digital signal to the adder circuit 68. Thus, the multiplier 66 cyclically outputs a frame of red signals (df*$\Delta R_{ij}$), and a frame of green signals (df*$\Delta G_{ij}$), with each of the signals exhibiting either zero or minus values.

When a digital signal (df*$\Delta R_{ij}$, df*$\Delta G_{ij}$) is input from the multiplier 66 to the adder circuit 68, a corresponding central digital image-pixel signal ($R_{ij}$, $G_{ij}$) is input from the one-pixel delay circuit PDL21 to the adder circuit 68 (FIG. 4). Namely, while the two frames of red and green signals (df*$\Delta R_{ij}$ and df*$\Delta G_{ij}$) are cyclically output from the multiplier 66 to the adder circuit 68, the two frames of red and green image-pixel signals ($R_{ij}$ and $G_{ij}$) are cyclically output from the one-pixel delay circuit PDL21 to the adder circuit 68. In the adder circuit 68, the frame of red image-pixel signals ($R_{ij}$) is added to the frame of red signals (df*$\Delta R_{ij}$), and the frame of green image-pixel signals ($G_{ij}$) is added to the frame of green signals (df*$\Delta G_{ij}$). Namely, in the adder circuit 68, the following calculations are performed:

$$R_{ij}=R_{ij}+df^*\Delta R_{ij}$$

$$G_{ij}=G_{ij}+df^*\Delta G_{ij}$$

As mentioned above, if $\Delta R_{ij} \geq 0$, the difference $\Delta R_{ij}$ is output as a zero value from the clipping circuit 64. Thus, if $\Delta R_{ij} \geq 0$, the red image-pixel signal $R_{ij}$ is output from the adder circuit 68 as it stands. If $\Delta R_{ij}<0$, the absolute value of the signal df*$\Delta R_{ij}$ is subtracted from the value of the red image-pixel signal $R_{ij}$ (df>0). Similarly, if $\Delta G_{ij} \geq 0$, the green image-pixel signal $G_{ij}$ is output from the adder circuit 68 as it stands. If $\Delta G_{ij}<0$, the absolute value of the green signal df*$\Delta G_{ij}$ is subtracted from the value of the green image-pixel signal $G_{ij}$.

Accordingly, when the differences $\Delta R_{ij}$ and $\Delta G_{ij}$ are minus, i.e. when the color image-pixel signals $R_{ij}$ and $G_{ij}$ are derived from a fine recess area X on a mucous membrane surface of, for example, a stomach or a colon, as conceptually shown in FIG. 1, the respective values of the red and green image-pixel signals $R_{ij}$ and $G_{ij}$ are decreased in proportion to a magnitude of the absolute values of the red and green signals df*$\Delta R_{ij}$ and df*$\Delta G_{ij}$. Therefore, when the simulated dye-spraying display mode is selected, a color image-pixel on the TV monitor 14, represented by the color image-pixel signals $R_{ij}$, $G_{ij}$, and $B_{ij}$, becomes bluish. Namely, a bluish endoscope image is observed on the TV monitor 14 as if an endoscope image, captured by the CCD image sensor 18, were sprayed with a blue-solution.

Also, when a difference ($\Delta R_{ij}$, $\Delta G_{ij}$) between a value of the central pixel signal ($R_{ij}$, $R_{ij}$) and an average value of some circumferential pixel signals surrounding the central pixel signals ($R_{ij}$, $R_{ij}$) is calculated by the difference-calculation circuit 62, the selection of some circumferential pixel signals is performed in accordance with the variation of the spatial frequency of an endoscope image to be reproduced on the TV monitor 14. Namely, the lower the spatial frequency of an endoscope image to be reproduced, the farther the circumferential pixel signals, to be selected for the calculation of the difference ($\Delta R_{ij}$, $\Delta G_{ij}$), from the central pixel signal ($R_{ij}$, $R_{ij}$). Thus, even if an endoscope image to be reproduced needs to be enlarged and/or even it the different types of video scopes 10 and 10' are selectively used, it is possible to properly perform the color-balance alteration process in the color-balance alteration circuit 44.

In this embodiment, for example, four settings of "10", "20", "40", and "80" to be assigned as the density factor "df" are previously prepared and stored in the EEPROM 33, and any one of the settings of "10", "20", "40", and "80" is manually assigned as the density factor "df", as stated in detail hereinafter. Also, each of the settings of "10", "20", "40", and "80" is variable and rewritable by operating the keyboard 58 through the system controller 32.

Figure 9:
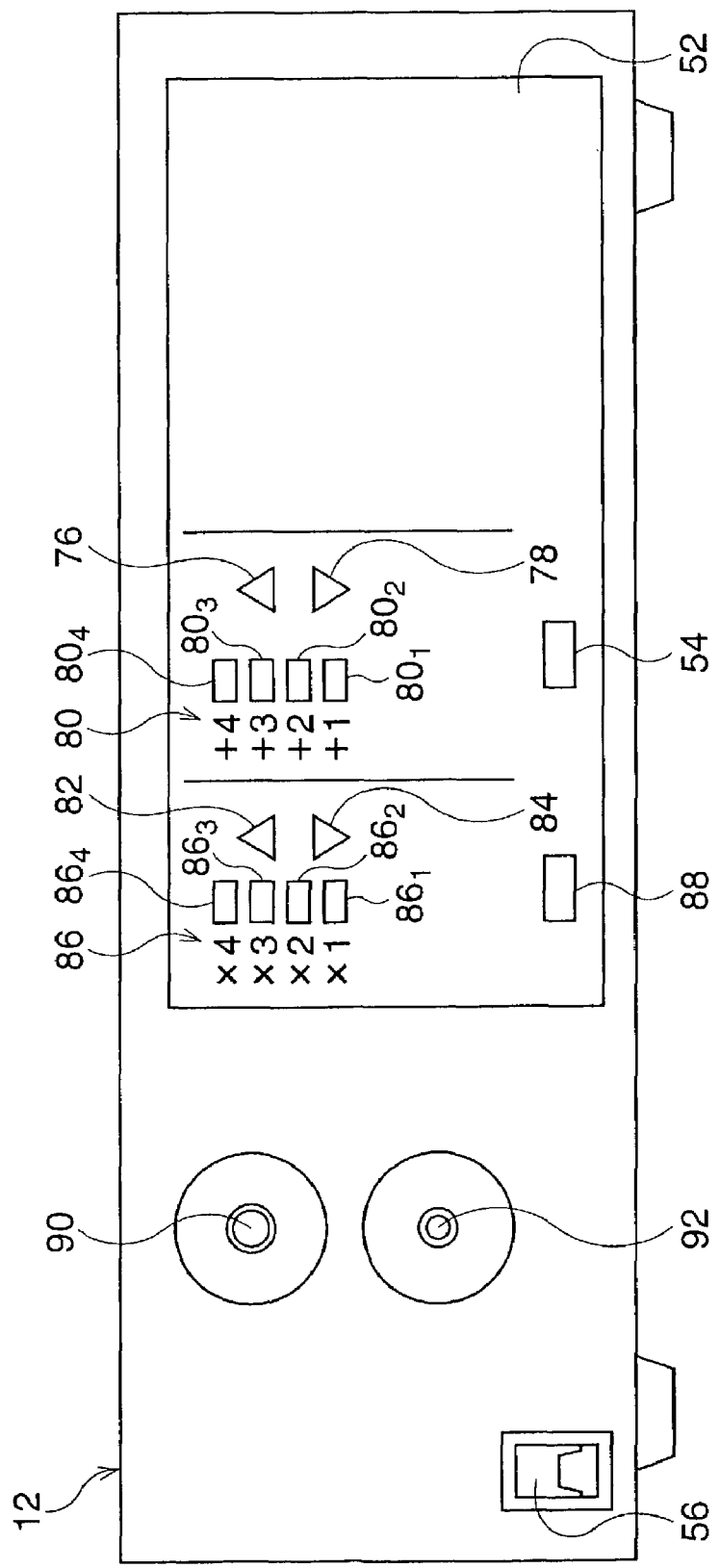
FIG. 9 is a front view of an image-signal processing unit forming a part of the electronic endoscope system shown in FIG. 1.

With reference to FIG. 9, the external appearance of the image-signal processing unit 12 is shown as a front view. As shown in this drawing, the display-mode selection switch 54 is provided on the front panel 52. Also, the power ON/OFF switch 56 is provided on the front wall of the housing.

As is apparent from FIG. 9, the display-mode selection switch 54 is associated with a density-increase switch 76 and a density-decrease switch 78 for manually and stepwisely varying the density factor "df", and a density-level indicator 80 including a column of window-like sections $80_1$, $80_2$, $80_3$, and $80_4$, to which respective density-level references "+1", "+2", "+3", and "+4" are respectively affixed. Each of the window-like sections $80_1$, $80_2$, $80_3$, and $80_4$ is formed of a semitransparent plate, which is associated with a light-emitting diode (LED).

Also, as shown in FIG. 9, the front panel 52 has a zoom-in switch 82 and a zoom-out switch 84 for manually operating the aforesaid electronic zooming system, and a zooming-level indicator 86 including a column of window-like sections $86_1$, $86_2$, $86_3$, and $86_4$, to which magnification-level references "×1", "×2", "×3", and "×4" are respectively affixed. Each of the window-like sections $86_1$, $86_2$, $86_3$, and $86_4$ is formed of a semitransparent plate, which is associated with a light-emitting diode (LED). The front panel 52 further has an initialization switch 88 associated with the zoom-level indicator 86.

Note, in FIG. 9, reference 90 indicates an electric socket for receiving an electric connector of the video scope (10, 10') so as to connect the CCD image sensor 18 to the CCD process circuit 36. Reference 92 indicates an optical socket for receiving an optical connector of the video scope so as to connect the light guide 22 to the light source device (24, 26, 28, and 30).

Figure 10:
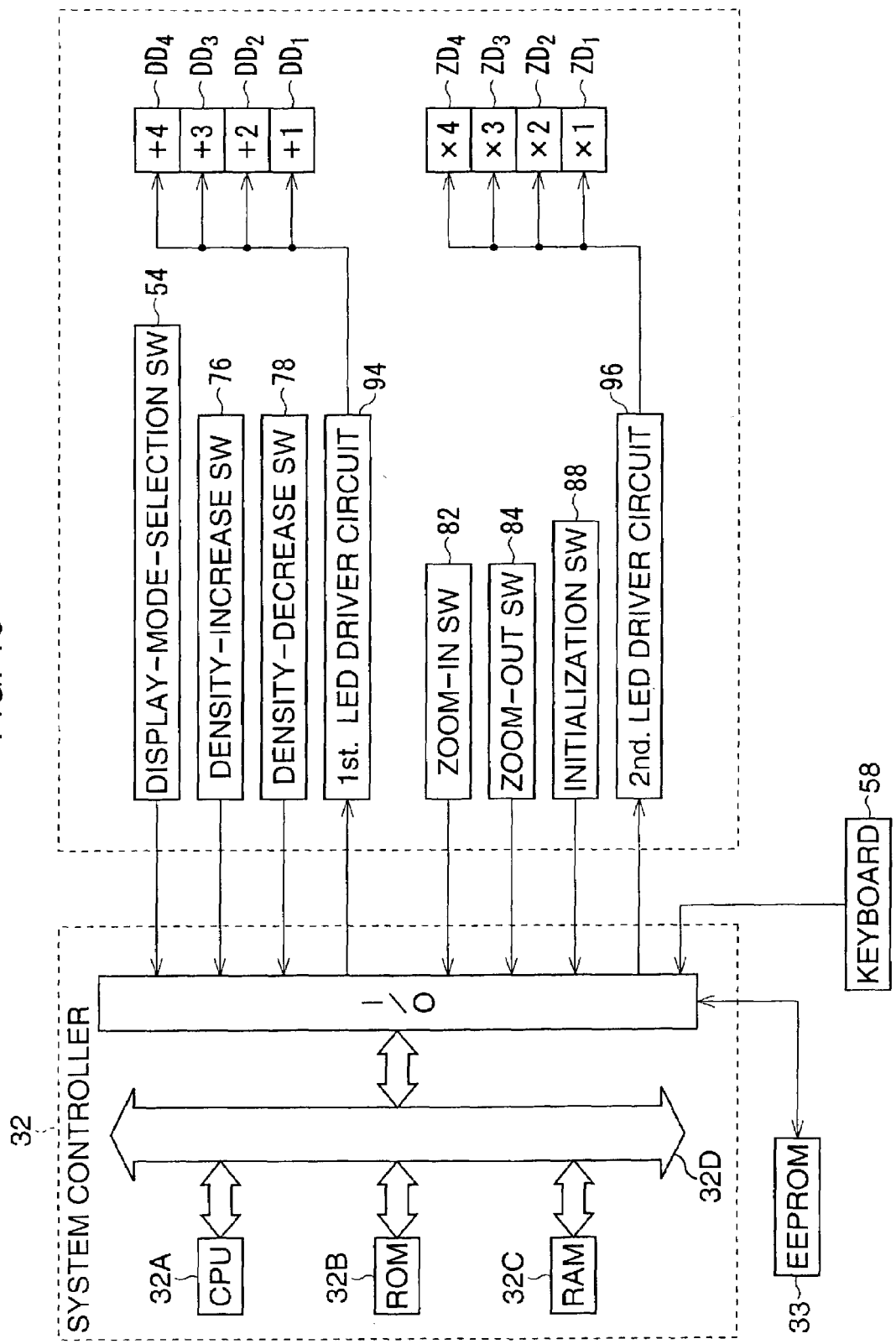
FIG. 10 is a block diagram between various switches provided on a front panel of the image-signal processing unit and a system controller provided therein.

With reference to FIG. 10, the relationships between the system controller 32 and the aforesaid various switches (54, 76, 78, 82, 84, and 88) are shown as a block diagram. In this drawing, the respective CPU, ROM, RAM, and I/O of the system controller 32 are indicated by references 32A, 32B, 32C, and 32D, and these elements are connected to each other through the buses. Also, in FIG. 10, respective references $DD_1$, $DD_2$, $DD_3$, and $DD_4$ indicate the LED's associated with the window-like sections $80_1$, $80_2$, $80_3$, and $80_4$, and respective references $ZD_1$, $ZD_2$, $ZD_3$, and $ZD_4$ indicate the LED's associated with the window-like sections $86_1$, $86_2$, $86_3$, and $86_4$. Further, in FIG. 10, reference 94 indicates a first LED driver circuit for selectively lighting the LED's $DD_1$, $DD_2$, $DD_3$, and $DD_4$, and reference 96 indicates a second LED driver circuit for selectively lighting the LED's $ZD_1$, $ZD_2$, $ZD_3$, and $ZD_4$.

Figure 11:
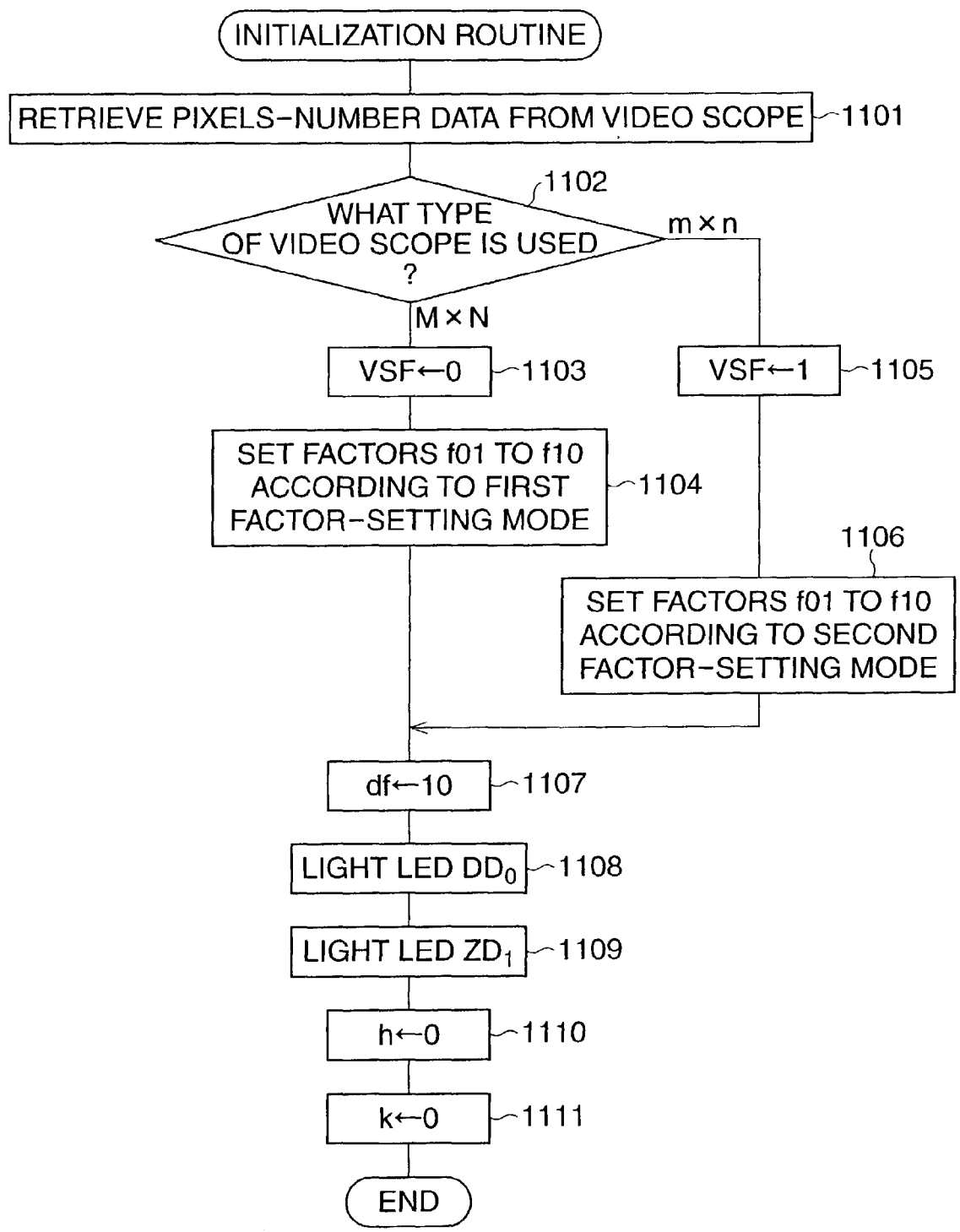
FIG. 11 shows a flowchart of an initialization routine executed in the system controller of the image-signal processing unit.

FIG. 11 shows a flowchart of an initialization routine executed in the system controller 32 used in the first embodiment. Note, this routine is only executed once by turning ON the power ON/OFF switch 56.

At step 1101, the system controller 32 retrieves pixel-number data from the ROM 60 of the video scope (10, 10') connected to the image-signal processing unit 12. Then, at step 1102, it is determined what type of video scope is used.

When it is confirmed that the video scope 10', featuring M×N image-pixel signals, is used, the control proceeds to step 1103, in which a video-scope-indication flag VSF is made to "0". Then, at step 1104, the factors f01 to f10 are set in accordance with the first factor-setting mode (1st. MODE) of the "FACTOR-SETTING TABLE" shown in FIG. 7. Namely, the respective settings of "1" and "−¼" are given to the factors f01 and f02, and the setting of "0" is given to all the remaining factors f02 to f10.

At step 1102, when it is confirmed that the video scope 10, featuring m×n image-pixel signals, is used, the control proceeds to step 1105, in which the video-scope-indication flag VSF is made to "1". Then, at step 1106, the factors f01 to f10 are set in accordance with the second factor-setting mode (2nd. MODE) of the "FACTOR-SETTING TABLE" shown in FIG. 7. Namely, the respective settings of "1" and "−¼" are given to the factors f01 and f03, and the setting of "0" is given to all the remaining factors f02, f04 to f10.

In either case, at step 1107, the density factor "df" is initialized to "10". Then, at step 1108, the LED $DD_0$ is lit, thereby indicating that the density-level "+1" has been selected as an initial density level. At step 1109, the LED $ZD_1$ is lit, thereby indicating that the one-power display mode has been selected as an initial magnifying power mode.

At step 1110, a counter "h" for managing manual operations of the zoom-in and zoom-out switches 82 and 84 is initialized to "0". Then, at step 1111, a counter "k" for managing manual operations of the density-increase and density-decrease switches 76 and 78 is initialized to "0". Thus, the initialization routine ends.

Figure 12:
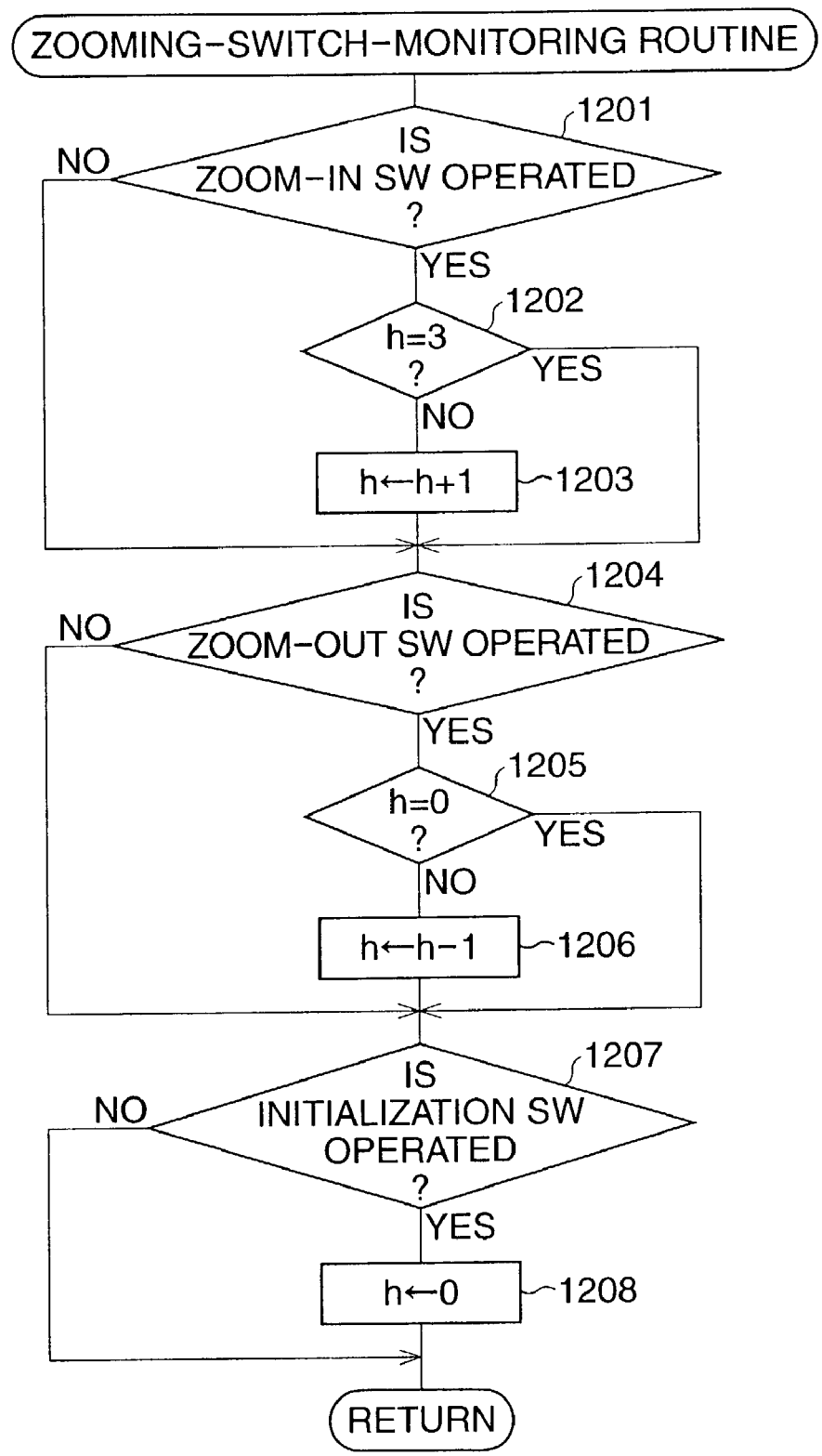
FIG. 12 shows a flowchart of a zooming-switch-monitoring routine executed in the system controller of the image-signal processing unit.

FIG. 12 shows a flowchart of a zooming-switch-monitoring routine, which is formed as a time-interruption routine executed in the system controller 32 at regular suitable intervals of, for example, 20 ms. The execution of this routine is started after the execution of the initialization routine of FIG. 11, and is repeated every 20 ms as long as the power ON/OFF switch 56 is turned ON.

At step 1201, it is monitored whether the zoom-in switch 82 has been operated. When the operation of the zoom-in switch 82 is confirmed, the control proceeds to step 1202, in which it is determined whether a count value of the counter "h" is equal to "3". If h<3, the control proceeds to step 1203, in which the count value of the counter "h" is incremented by "1". Then, the control proceeds to step 1204. At step 1202, if h=3, the control skips step 1203 and goes to step 1204. Also, at step 1201, when the operation of the zoom-in switch 82 is not confirmed, the control skips steps 1202 and 1203 and goes to step 1204. In short, whenever the zoom-in switch 82 is operated, the count value of the counter "h" is incremented by "1", but the operation of the zoom-in switch 82 is ignored when the count value of the counter "h" reaches "3".

At step 1204, it is monitored whether the zoom-out switch 84 has been operated. When the operation of the zoom-out switch 84 is confirmed, the control proceeds to step 1205, in which it is determined whether the count value of the counter "h" is equal to "0". If h>0, the control proceeds to step 1206, in which the count value of the counter "h" is decremented by "1". Then, the control proceeds to step 1207. At step 1205, if h=0, the control skips step 1206 and goes to step 1207. Also, at step 1204, when the operation of the zoom-out switch 84 is not confirmed, the control skips steps 1205 and 1206 and goes to step 1207. In short, whenever the zoom-out switch 84 is operated, the count value of the counter "h" is decremented by "1", but the operation of the zoom-out switch 84 is ignored when the count value of the counter "h" reaches "0".

At step 1207, it is monitored whether the initialization switch 88 has been operated. When the operation of the switch 88 is confirmed, the control proceeds to step 1208, in which the count value of counter "h" is initialized to "0".

Figure 13:
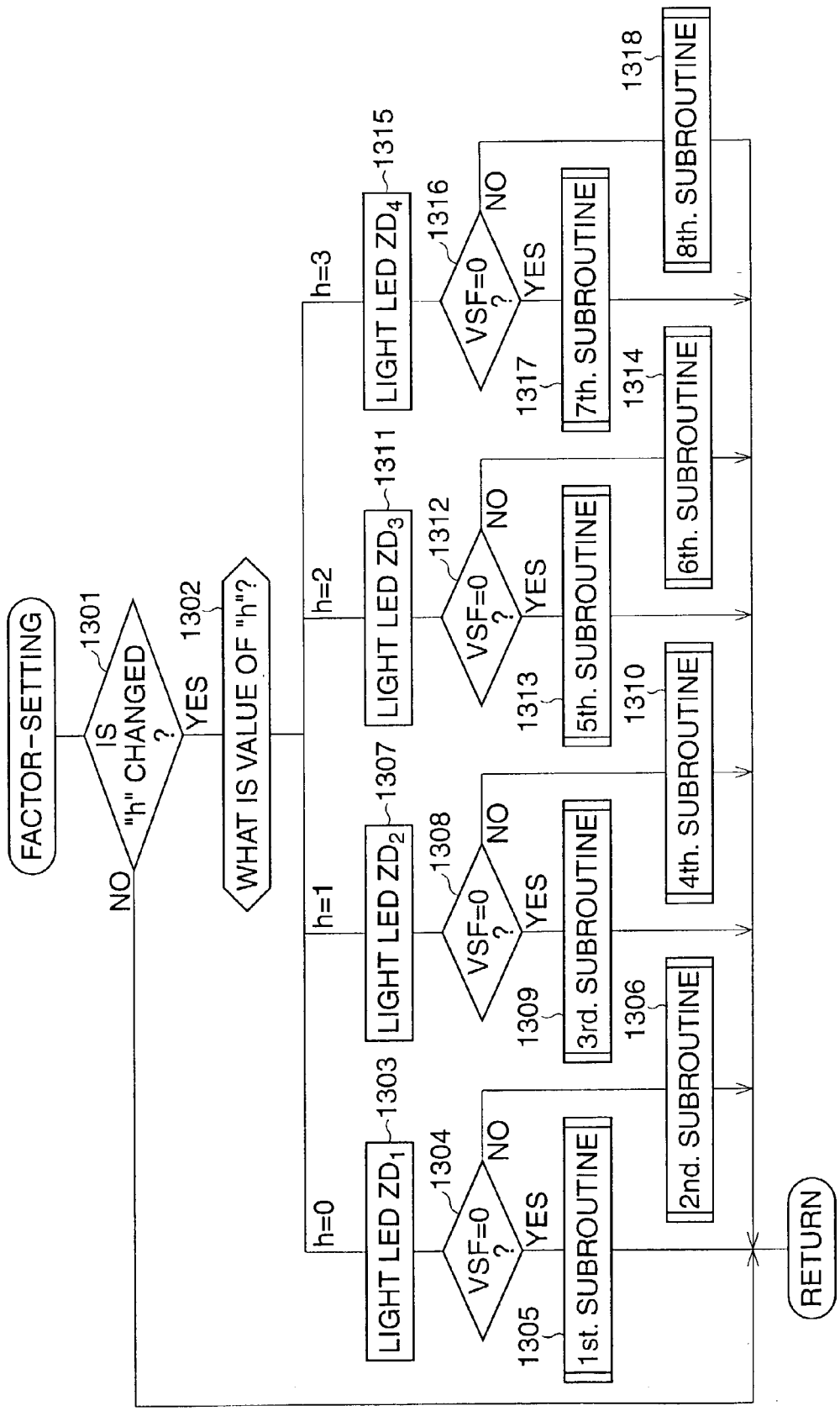
FIG. 13 shows a flowchart of a factor-setting routine executed in the system controller of the image-signal processing unit.

FIG. 13 shows a flowchart of a factor-setting routine, which is formed as a time-interruption routine executed in the system controller 32 at regular suitable intervals of, for example, 20 ms. The execution of this routine is started after the execution of the initialization routine of FIG. 11, and is repeated every 20 ms as long as the power ON/OFF switch 56 is turned ON.

At step 1301, it is monitored whether the count value of the counter "h" has been changed by operating any one of the zoom-in switch 82, the zoom-out switch 84, and the initialization switch 88. When the change in the count value of the counter "h" is not confirmed, the routine immediately ends. Thereafter, although the routine is repeatedly executed every 20 ms, there is no progress until the change in the count value of the counter "h" is confirmed.

At step 1301, when the change of the count value of the counter "h" is confirmed, the control proceeds to step 1302, in which the count value of the counter "h" is determined.

If h=0, the control proceeds to step 1303, in which the LED $ZD_1$ is lit, thereby indicating that the one-power display mode "×1" has been selected. Then, at step 1304, it is determined whether the video-scope-indication flag VSF is either "0" or "1".

Figure 14:
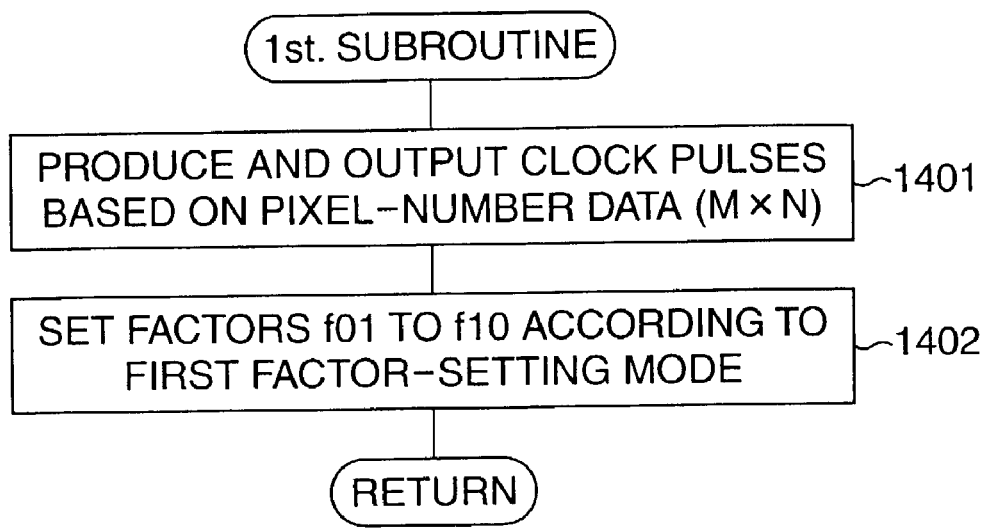
FIG. 14 shows a flowchart of a first subroutine executed in the factor-setting routine.

If VSF=0, i.e. if the video scope, featuring M×N image-pixel signals, is used, the control proceeds to step 1305, in which a first subroutine, shown in FIG. 14, is executed. Namely, the timing controller 34 produces and outputs the various series of clock pulses having given frequencies, based on the pixel-number data (M×N), whereby the frames of M×N image-pixel signals, obtained from the video scope 10' (M×N), can be properly processed in the image-signal processor (step 1401 in FIG. 14), such that the endoscope image, sensed by the video scope 10' (M×N), is reproduced on the TV monitor 14 at the magnifying power of 1. Then, the factors f01 to f10 are set in accordance with the first factor-setting mode (1st. MODE) of the "FACTOR-SETTING TABLE" shown in FIG. 7 (step 1402 in FIG. 14).

Figure 15:
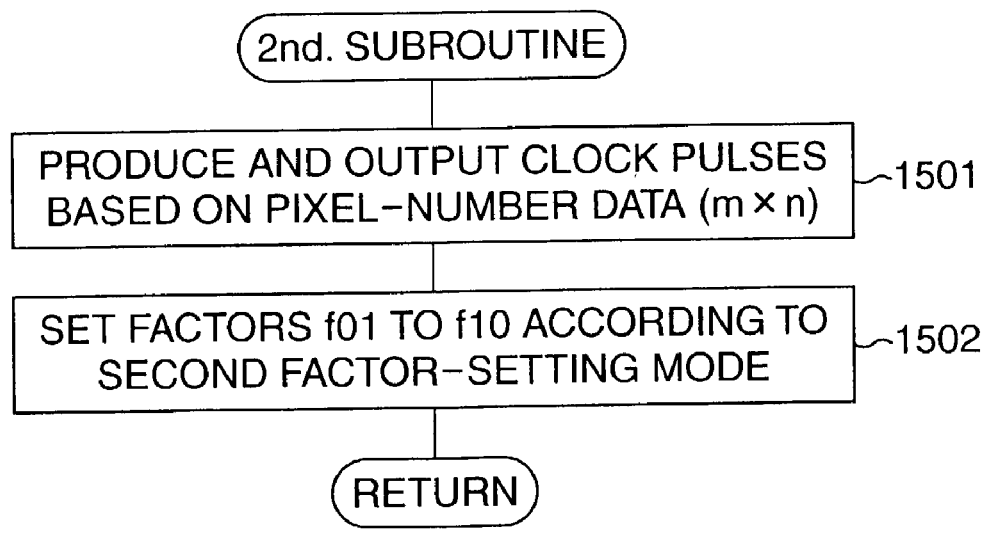
FIG. 15 shows a flowchart of a second subroutine executed in the factor-setting routine.

At step 1304, if VSF=1, i.e. if the video scope 10, featuring m×n image-pixel signals, is used, the control proceeds from step 1304 to step 1306, in which a second subroutine, shown in FIG. 15, is executed. Namely, the timing controller 34 produces and outputs the various series of clock pulses having given frequencies, based on the pixel-number data (m×n), whereby frames of m×n image-pixel signals, obtained from the video scope 10 (m×n), can be properly processed in the image-signal processor (step 1501 in FIG. 15), such that the endoscope image, sensed by the video scope 10 (m×n), is reproduced on the TV monitor 14 at the magnifying power of 1. Then, the factors f01 to f10 are set in accordance with the second factor-setting mode (2nd. MODE) of the "FACTOR-SETTING TABLE" shown in FIG. 7 (step 1502 in FIG. 15).

At step 1302, if h=1, the control proceeds to step 1307, in which the LED ZD$_2$ is lit, thereby indicating that the two-power display mode "×2" has been selected. Then, at step 1308, it is determined whether the video-scope-indication flag VSF is either "0" or "1".

Figure 16:
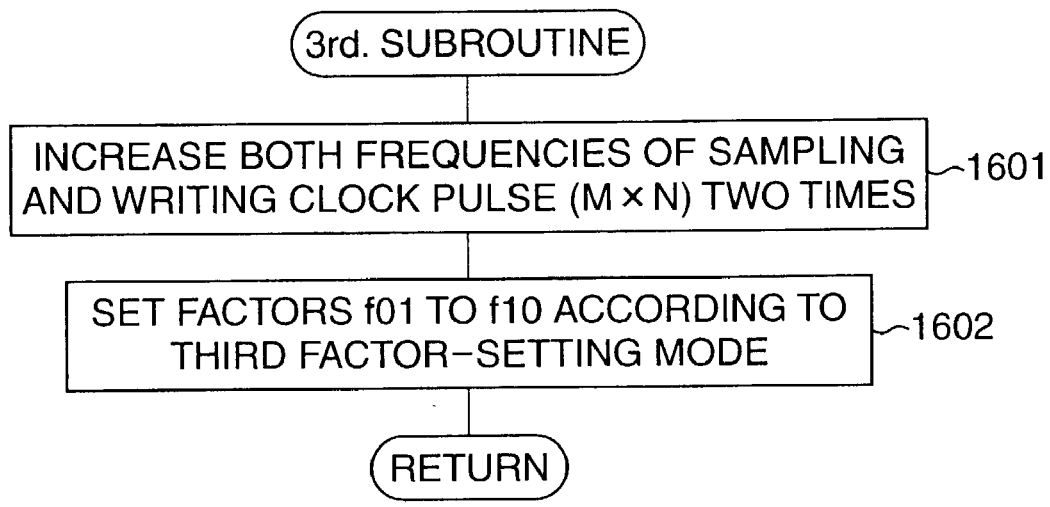
FIG. 16 shows a flowchart of a third subroutine executed in the factor-setting routine.

If VSF=0, i.e. if the video scope 10', featuring M×N image-pixel signals, is used, the control proceeds to step 1309, in which a third subroutine, shown in FIG. 16, is executed. Namely, both the frequency of the sampling clock pulses and the frequency of the writing clock pulses, output from the timing controller 34 to the A/D converter 38 and the frame memory 40, are increased two times (step 1601 in FIG. 16), such that an endoscope image, sensed by the video scope 10' (M×N), is reproduced on the TV monitor 14 at the magnifying power of 2. Then, the factors f01 to f10 are set in accordance with the third factor-setting mode (3rd. MODE) of the "FACTOR-SETTING TABLE" shown in FIG. 7 (step 1602 in FIG. 16).

Figure 17:
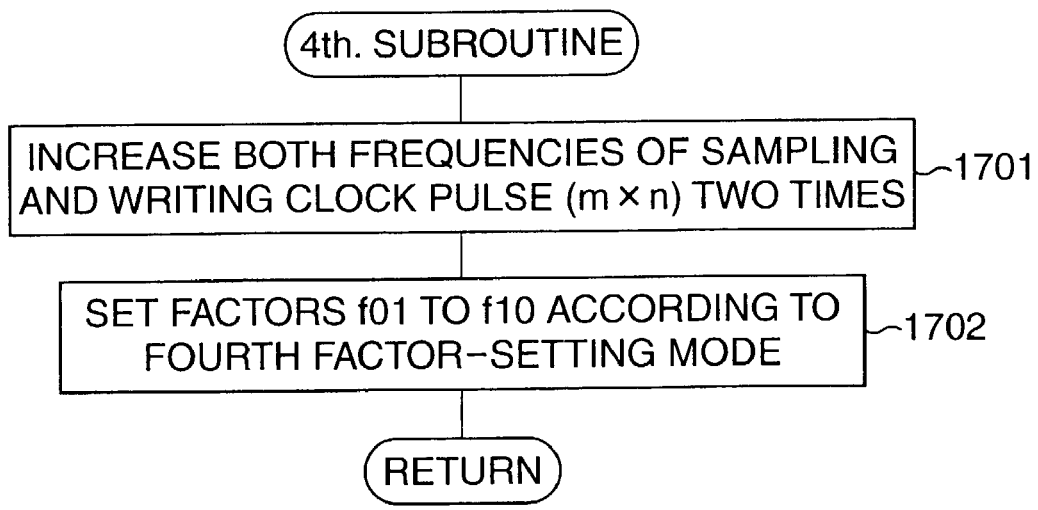
FIG. 17 shows a flowchart of a fourth subroutine executed in the factor-setting routine.

At step 1308, if VSF=1, i.e. if the video scope 10, featuring m×n image-pixel signals, is used, the control proceeds to step 1310, in which a fourth subroutine, shown in FIG. 17, is executed. Namely, both the frequency of the sampling clock pulses and the frequency of the writing clock pulses, output from the timing controller 34 to the A/D converter 38 and the frame memory 40, are increased two times (step 1701 in FIG. 17), such that an endoscope image, sensed by the video scope 10 (m×n), is reproduced on the TV monitor 14 at the magnifying power of 2. Then, the factors f01 to f10 are set in accordance with the fourth factor-setting mode (4th. MODE) of the "FACTOR-SETTING TABLE" shown in FIG. 7 (step 1702 in FIG. 17).

At step 1302, if h=2, the control proceeds to step 1311, in which the LED ZD$_3$ is lit, thereby indicating that the three-power display mode "×3" has been selected. Then, at step 1312, it is determined whether the video-scope-indication flag VSF is either "0" or "1".

Figure 18:
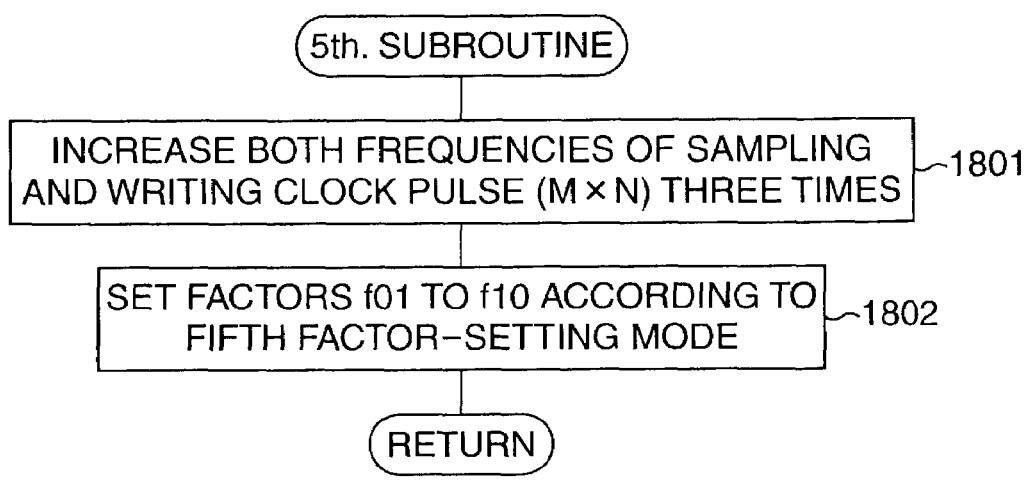
FIG. 18 shows a flowchart of a fifth subroutine executed in the factor-setting routine.

If VSF=0, i.e. if the video scope 10', featuring M×N image-pixel signals, is used, the control proceeds to step 1313, in which a fifth subroutine, shown in FIG. 18, is executed. Namely, both the frequency of the sampling clock pulses and the frequency of the writing clock pulses, output from the timing controller 34 to the A/D converter 38 and the frame memory 40, are increased three times (step 1801 in FIG. 18), such that an endoscope image, sensed by the video scope 10' (M×N), is reproduced on the TV monitor 14 at the magnifying power of 3. Then, the factors f01 to f10 are set in accordance with the fifth factor-setting mode (5th. MODE) of the "FACTOR-SETTING TABLE" shown in FIG. 7 (step 1802 in FIG. 18).

Figure 19:
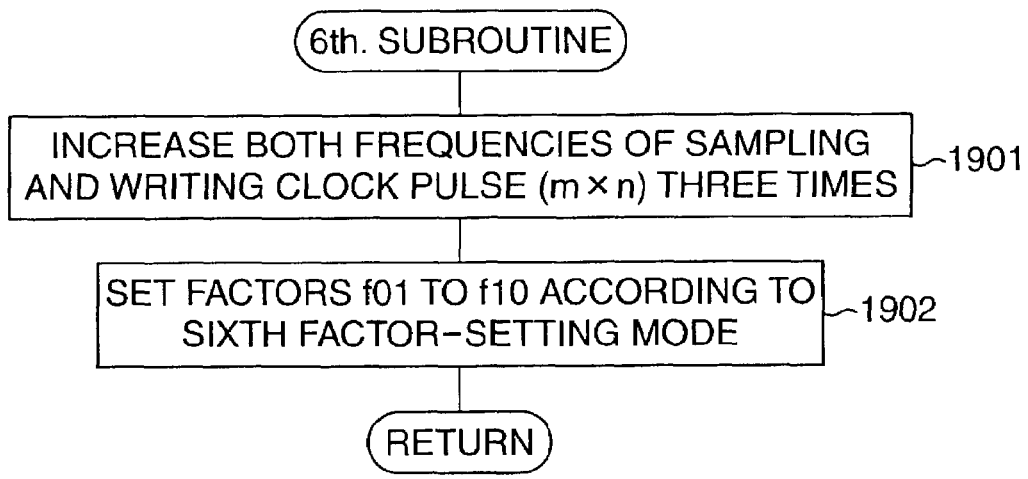
FIG. 19 shows a flowchart of a sixth subroutine executed in the factor-setting routine.

At step 1312, if VSF=1, i.e. if the video scope 10, featuring m×n image-pixel signals, is used, the control proceeds to step 1314, in which a sixth subroutine, shown in FIG. 19, is executed. Namely, both the frequency of the sampling clock pulses and the frequency of the writing clock pulses, output from the timing controller 34 to the A/D converter 38 and the frame memory 40, are increased three times (step 1901 in FIG. 19), such that an endoscope image, sensed by the video scope 10 (m×n), is reproduced on the TV monitor 14 at the magnifying power of 3. Then, the factors f01 to f10 are set in accordance with the sixth factor-setting mode (6th. MODE) of the "FACTOR-SETTING TABLE" shown in FIG. 7 (step 1902 in FIG. 19).

At step 1302, if h=3, the control proceeds to step 1315, the LED ZD$_4$ is lit, thereby indicating that the four-power display mode "×4" has been selected. Then, at step 1316, it is determined whether the video-scope-indication flag VSF is either "0" or "1".

Figure 20:
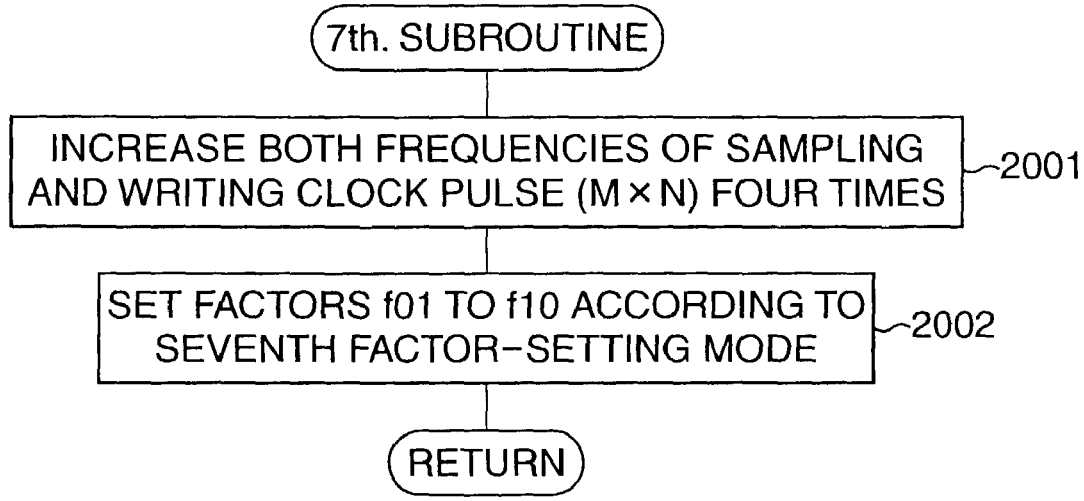
FIG. 20 shows a flowchart of a seventh subroutine executed in the factor-setting routine.

If VSF=0, i.e. if the video scope 10', featuring M×N image-pixel signals, is used, the control proceeds to step 1317, in which a seventh subroutine, shown in FIG. 20, is executed. Namely, both the frequency of the sampling clock pulses and the frequency of the writing clock pulses, output from the timing controller 34 to the A/D converter 38 and the frame memory 40, are increased four times (step 2001 in FIG. 20), such that an endoscope image, sensed by the video scope 10' (M×N), is reproduced on the TV monitor 14 at the magnifying power of 4. Then, the factors f01 to f10 are set in accordance with the seventh factor-setting mode (7th. MODE) of the "FACTOR-SETTING TABLE" shown in FIG. 7 (step 2002 in FIG. 20).

Figure 21:
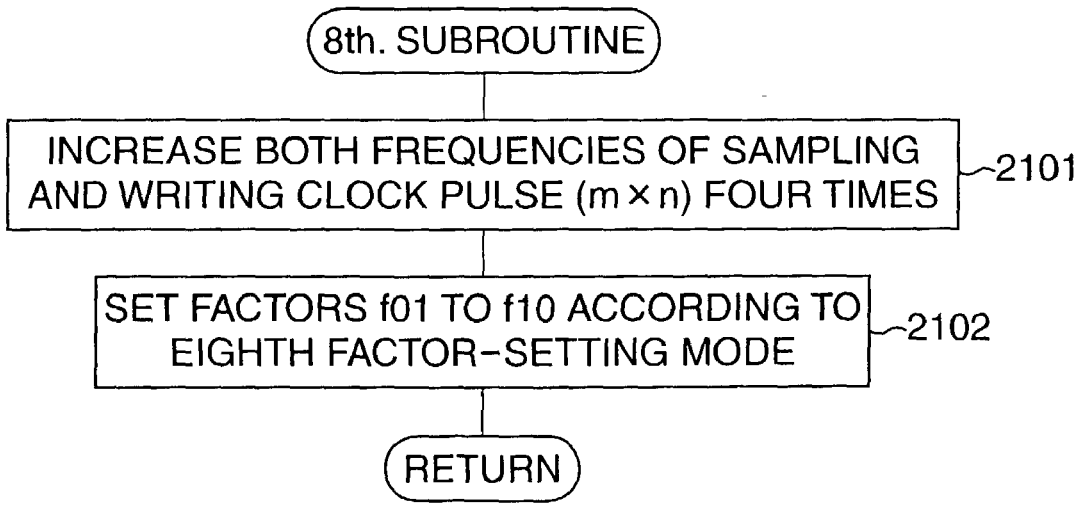
FIG. 21 shows a flowchart of an eighth subroutine executed in the factor-setting routine.

At step 1316, if VSF=1, i.e. if the video scope 10, featuring m×n image-pixel signals, is used, the control proceeds to step 1318, in which an eighth subroutine, shown in FIG. 21, is executed. Namely, both the frequency of the sampling clock pulses and the frequency of the writing clock pulses, output from the timing controller 34 to the A/D converter 38 and the frame memory 40, are increased four times (step 2101 in FIG. 21), such that an endoscope image, sensed by the video scope 10 (m×n), is reproduced on the TV monitor 14 at the magnifying power of 4. Then, the factors f01 to f10 are set in accordance with the eighth factor-setting mode (8th. MODE) of the "FACTOR-SETTING TABLE" shown in FIG. 7 (step 2102 in FIG. 21).

Figure 22:
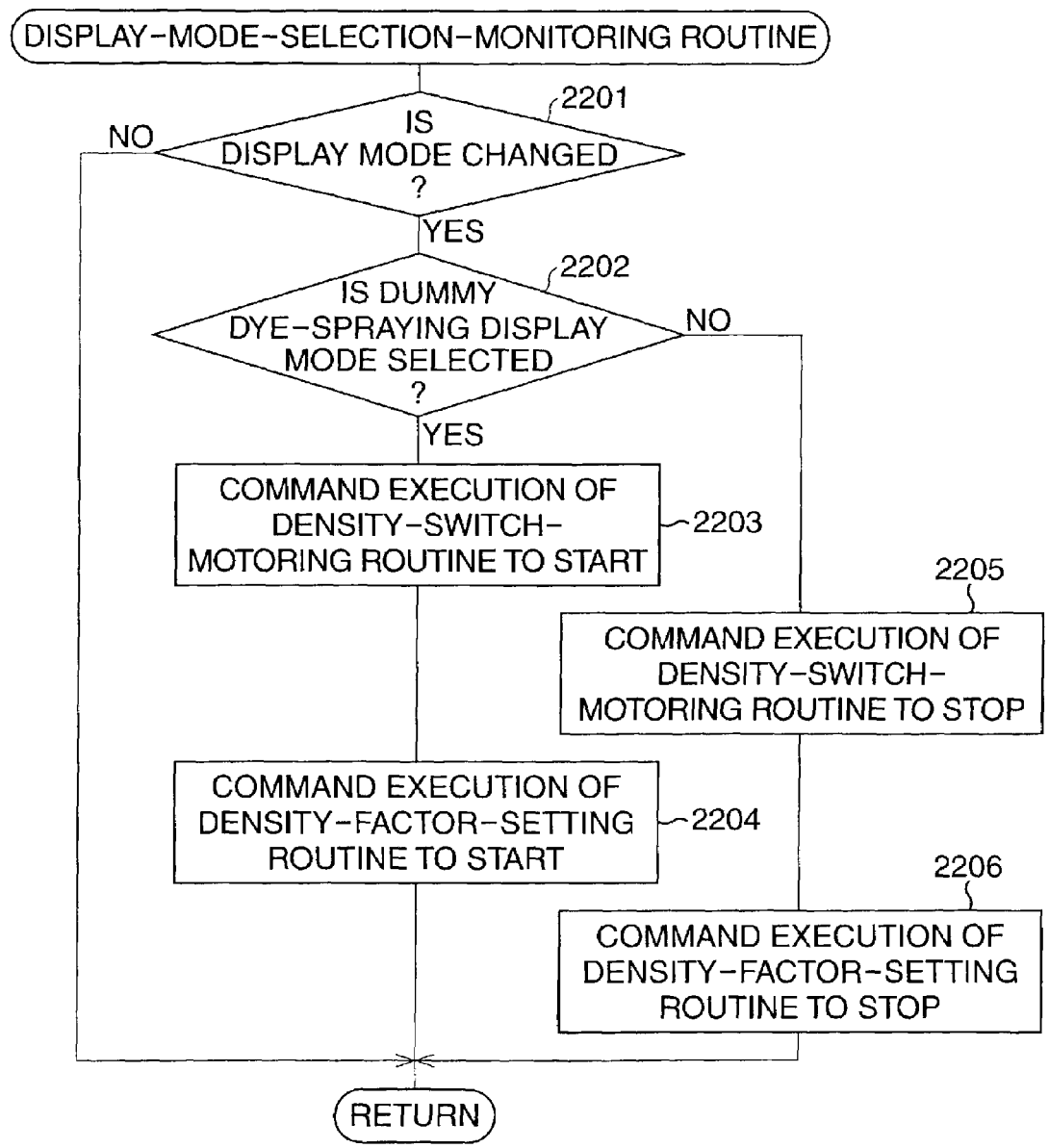
FIG. 22 shows a flowchart of a display-mode-selection-monitoring routine executed in the system controller of the image-signal processing unit.

FIG. 22 shows a flowchart of a display-mode-selection-monitoring routine, which is formed as a time-interruption routine executed in the system controller 32 at regular suitable intervals of, for example, 20 ms. The execution of this routine is started after the execution of the initialization routine of FIG. 11, and is repeated every 20 ms as long as the power ON/OFF switch 56 is turned ON.

At step 2201, it is monitored whether either the usual display mode or the simulated dye-spraying display mode has been changed to the other display mode by operating either the display mode selection switch 54 or the corresponding function key on the keyboard 58. When the change of the display mode is not confirmed, the routine immediately ends. Although the routine is repeatedly executed every 20 ms, there is no progress until a change in the display mode is confirmed.

At step 2201, when it is confirmed that the display mode has been changed, the control proceeds to step 2202, in which it is determined whether the simulated dye-spraying display mode has been selected. When the selection of the simulated dye-spraying display mode is confirmed, the control proceeds to step 2203, in which starting the execution of a density-switch-monitoring routine is commanded by the system controller 32. Note, the density-switch-monitoring routine is explained hereinafter with reference to FIG. 23. Then, at step 2204, starting the execution of a density-factor-setting routine is commanded by the system controller 32. Note, the density-factor-setting routine is explained hereinafter with reference to FIG. 24.

At step 2202, when the selection of the simulated dye-spraying display mode is not confirmed, i.e. when it is confirmed that the usual display mode has been selected, the control proceeds from step 2202 to step 2205, in which stopping the execution of the density-switch-monitoring routine is commanded by the system controller 32. Then, at step 2206, stopping the execution of the density-factor-setting routine is commanded by the system controller 32.

Figure 23:
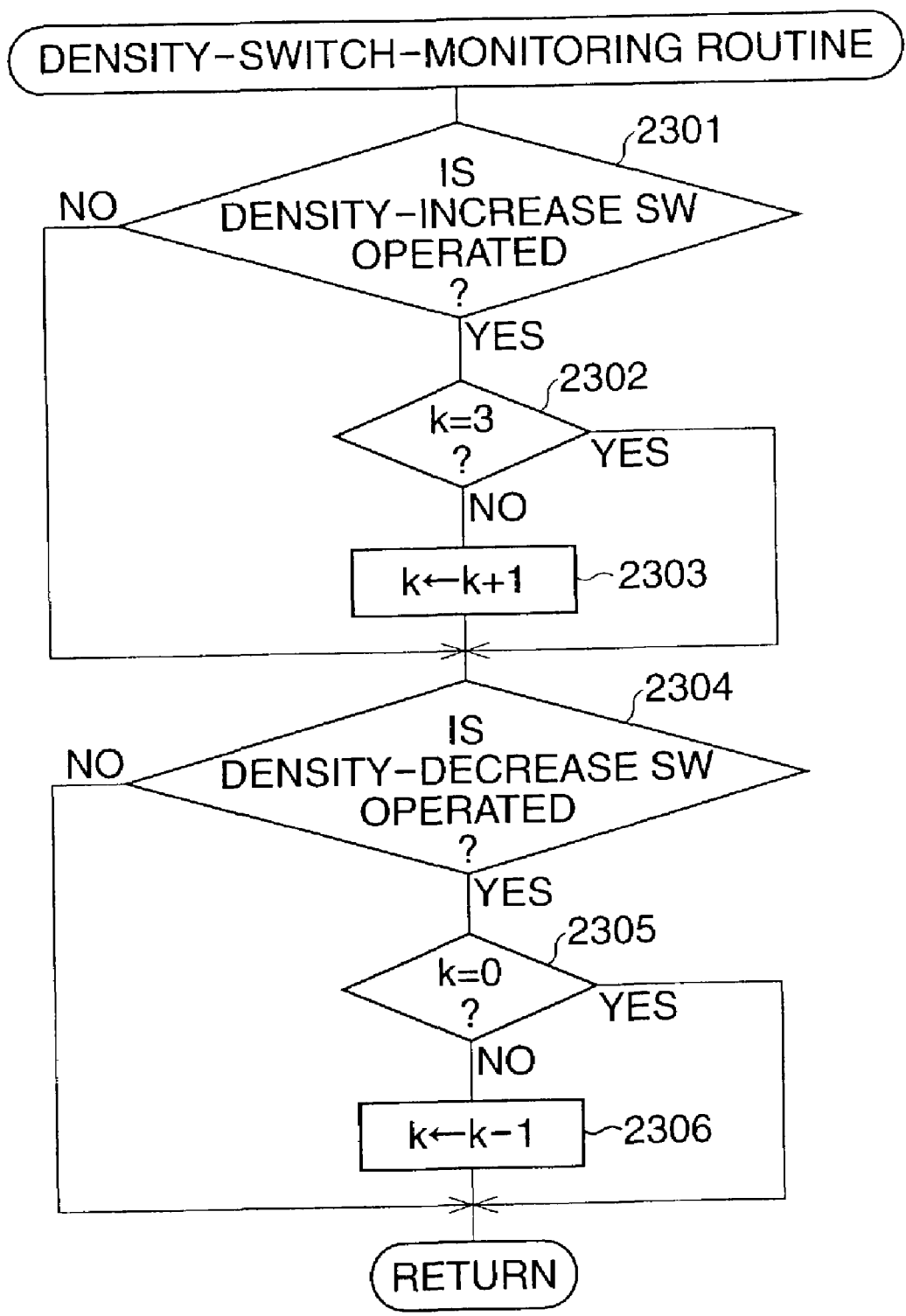
FIG. 23 shows a flowchart of a density-switch-monitoring routine executed in the system controller of the image-signal processing unit.

FIG. 23 shows a flowchart of the density-switch-monitoring routine, referred to in steps 2203 and 2205 of FIG. 22, which is formed as a time-interruption routine executed in the system controller 32 at regular suitable intervals of, for example, 20 ms.

At step 2301, it is monitored whether the density-increase switch 76 has been operated. When the operation of the density-increase switch 76 is confirmed, the control proceeds to step 2302, in which it is determined whether the count value of the counter "k" is equal to "3". If k<3, the control proceeds to step 2303, in which the count value of the counter "k" is incremented by "1". Then, the control proceeds to step 2304. At step 2302, if k=3, the control skips step 2302 to step 2304. Also, at step 2301, when the operation of the density-increase switch 76 is not confirmed, the control skips steps 2302 and 2303 to step 2304. In short, whenever the density-increase switch 76 is operated, the count value of the counter "k" is incremented by "1", but the operation of the density-increase switch 76 is ignored when the count value of the counter "k" reaches "3".

At step 2304, it is monitored whether the density-decrease switch 78 has been operated. When the operation of the density-decrease switch 78 is confirmed, the control proceeds to step 2305, in which it is determined whether the count value of the counter "k" is equal to "0". If k>0, the control proceeds to step 2306, in which the count value of the counter "k" is decremented by "1". At step 2305, if k=0, the routine ends. In short, whenever the density-decrease switch 78 is operated, the count value of the counter "k" is decremented by "1", but the operation of the density-decrease switch 78 is ignored when the count value of the counter "k" reaches "0".

Figure 24:
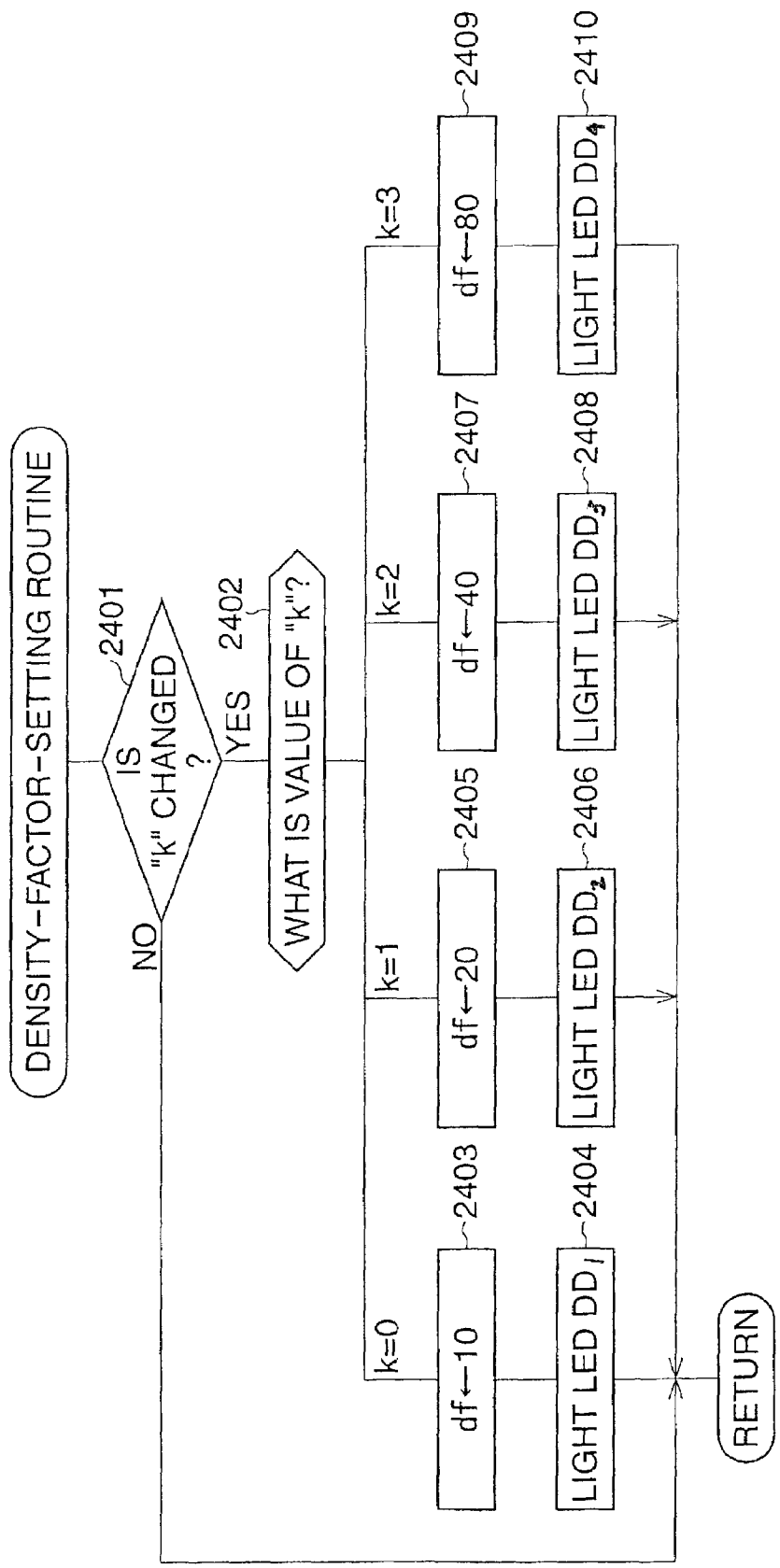
FIG. 24 shows a flowchart of a density-factor-setting routine executed in the system controller of the image-signal processing unit.

FIG. 24 shows a flowchart of the density-factor-setting routine, referred to in steps 2204 and 2206 of FIG. 22, which is formed as a time-interruption routine executed in the system controller 32 at regular suitable intervals of, for example, 20 ms.

At step 2401, it is monitored whether the count value of the counter "k" has been changed by operating either the density-increase switch 76 or the density-decrease switch 78. When the change of the count value of the counter "k" is not confirmed, the routine immediately ends. Thereafter, although the routine is repeatedly executed every 20 ms, there is no progress until the change of the count value of the counter "k" is confirmed.

At step 2401, when the change of the count value of the counter "k" is confirmed, the control proceeds to step 2402, in which it is determined what is the count value of the counter "k".

If k=0, the control proceeds to step 2403, in which the setting of "10" is retrieved from the EEPROM 33, and is then given to the density factor "df" in the multiplier 86 at a proper timing. Namely, as soon as a frame of digital signals is completely output from the clipping circuit 64, the setting of "10" is given to the density factor "df" in the multiplier 86. Then, at step 2404, the LED $DD_1$ is lit, thereby indicating that the density level "+1" has been selected.

If k=1, the control proceeds to step 2405, in which the setting of "20" is retrieved from the EEPROM 33, and is then used for the density factor "df" in the multiplier 86 at the proper timing. Then, at step 2406, the LED $DD_2$ is lit, thereby indicating that the density level "+2" has been selected.

If k=2, the control proceeds to step 2407, in which the setting of "40" is retrieved from the EEPROM 33, and is then used for the density factor "df" in the multiplier 86 at the proper timing. Then, at step 2408, the LED $DD_3$ is lit, thereby indicating that the density level "+3" has been selected.

If k=3, the control proceeds to step 2409, in which the setting of "80" is retrieved from the EEPROM 33, and is then used for the density factor "df" in the multiplier 86 at the proper timing. Then, at step 2410, the LED $DD_4$ is lit, thereby indicating that the density level "+4" has been selected.

In the first embodiment, the switching-circuit 42 may be optionally omitted from the image-signal processor provided in the image-signal processing unit 12. In this case, the frames of red, green, and blue image-pixel signals ($R_{ij}$, $G_{ij}$, and $B_{ij}$) are cyclically fed from the frame memory 40 to the color-balance alteration circuit 44, regardless of the selection of either the usual display mode or the simulated dye-spraying display mode, provided that the setting of "0" is forcibly given to the density factor "df" in the multiplier 66 during the selection of the usual display mode. Namely, the frames of red, green, and blue image-pixel signals ($R_{ij}$, $G_{ij}$, and $B_{ij}$) can pass through the color-balance alteration circuit 44 without being subjected to any color-balance alteration process, due to the setting of "0" for the density factor "df" in the multiplier 66.

Also, in the case where the switching-circuit 42 is omitted from the image-signal processor, it is necessary to cyclically give the setting of "0" to the density factor "df" during the selection of the simulated dye-spraying display mode, such that the frame of blue digital image-pixel signals ($B_{ij}$) can pass through the color-balance alteration circuit 44 without being subjected to any color-balance alteration process.

Figure 25:
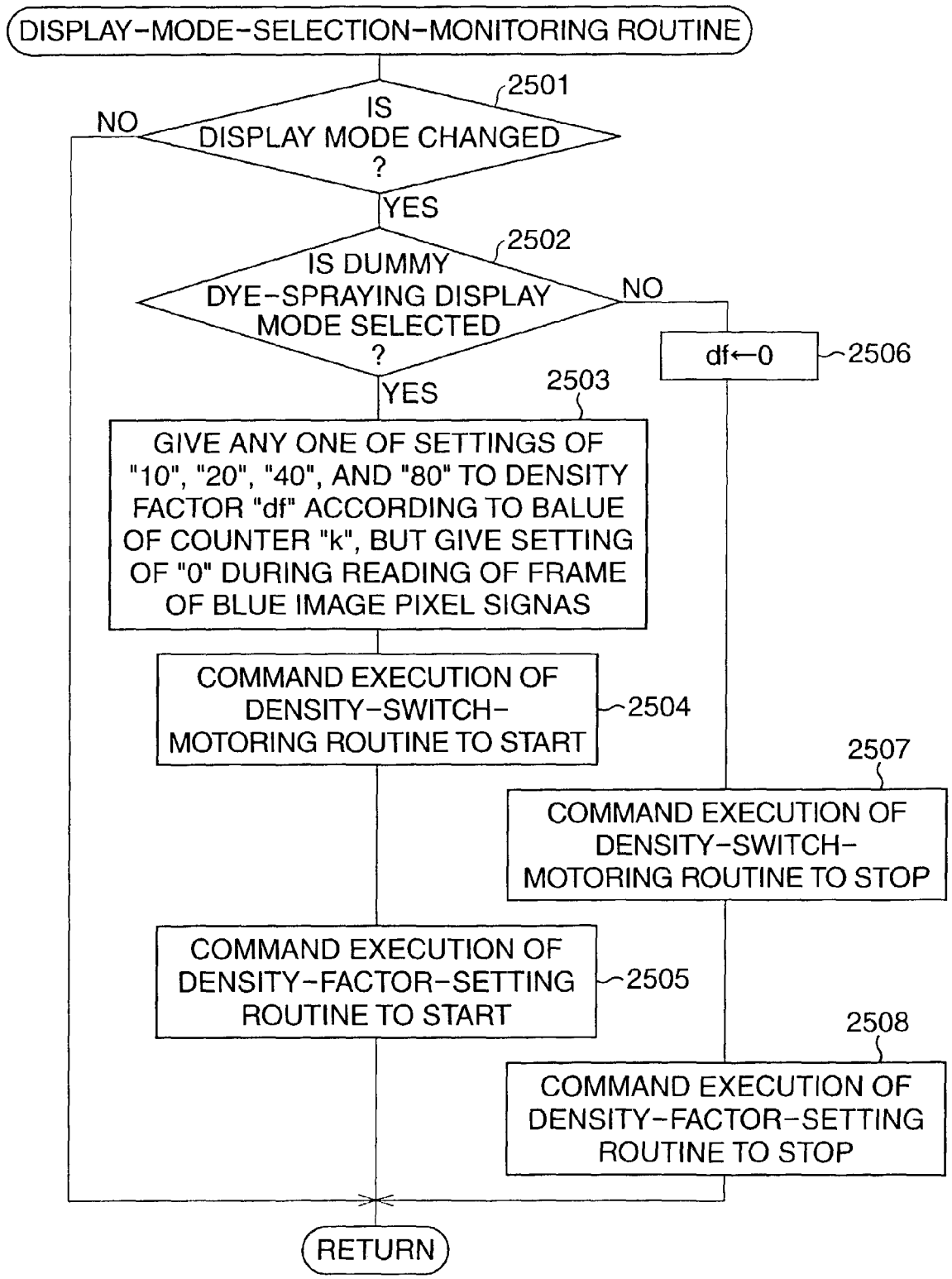
FIG. 25 shows a flowchart of a display-mode-selection-monitoring routine, similar to FIG. 22, executed in a modification of the first embodiment.

FIG. 25 shows a flowchart of a display-mode-selection-monitoring routine, which is executed as a substitute for the display-mode-selection-monitoring routine of FIG. 22 in the system controller 32 when the switching-circuit 42 is omitted from the image-signal processor.

At step 2501, it is monitored whether either the usual display mode or the simulated dye-spraying display mode has been changed to the other display mode by operating either the display mode selection switch 54 or the corresponding function key on the keyboard 58. When a change in the display mode is not confirmed, the routine immediately ends. Although the routine is repeatedly executed every 20 ms, there is no progress until a change in the display mode is confirmed.

At step 2501, when it is confirmed that the display mode has been changed, the control proceeds to step 2502, in which it is determined whether the simulated dye-spraying display mode has been selected. When the selection of the simulated dye-spraying display mode is confirmed, the control proceeds to step 2503, in which any one of the settings of "10", "20", "40", and "80" is used for the density factor "df" in the multiplier 68 in accordance with the count value of the counter k, but the setting of "0" is used for the density factor "df" during the reading of a frame of blue digital image-pixel signals ($B_{ij}$) from the frame memory 40. Of course, the setting of "0" for the density factor "df" is performed at the proper timing such that the frame of blue digital image-pixel signals ($B_{ij}$) passes through the color-balance alteration circuit 44 as they stand, without being subjected to any color-balance alteration process by the color-balance alteration circuit 44.

At step 2504, starting an execution of the density-switch-monitoring routine of FIG. 23 is commanded by the system controller 32. Then, at step 2505, starting an execution of the density-factor-setting routine of FIG. 24 is commanded by the system controller 32.

At step 2502, when the selection of the simulated dye-spraying display mode is not confirmed, i.e. when it is confirmed that the usual display mode has been selected, the control proceeds from step 2502 to step 2506, in which the setting of "0" is forcibly used for the density factor "df" in the multiplier 68 regardless of the count value of the counter k.

At step 2507, stopping the execution of the density-switch-monitoring routine of FIG. 23 is commanded by the system controller 32. Then, at step 2508, stopping the execution of the density-factor-setting routine of FIG. 24 is commanded by the system controller 32.

Figure 26:
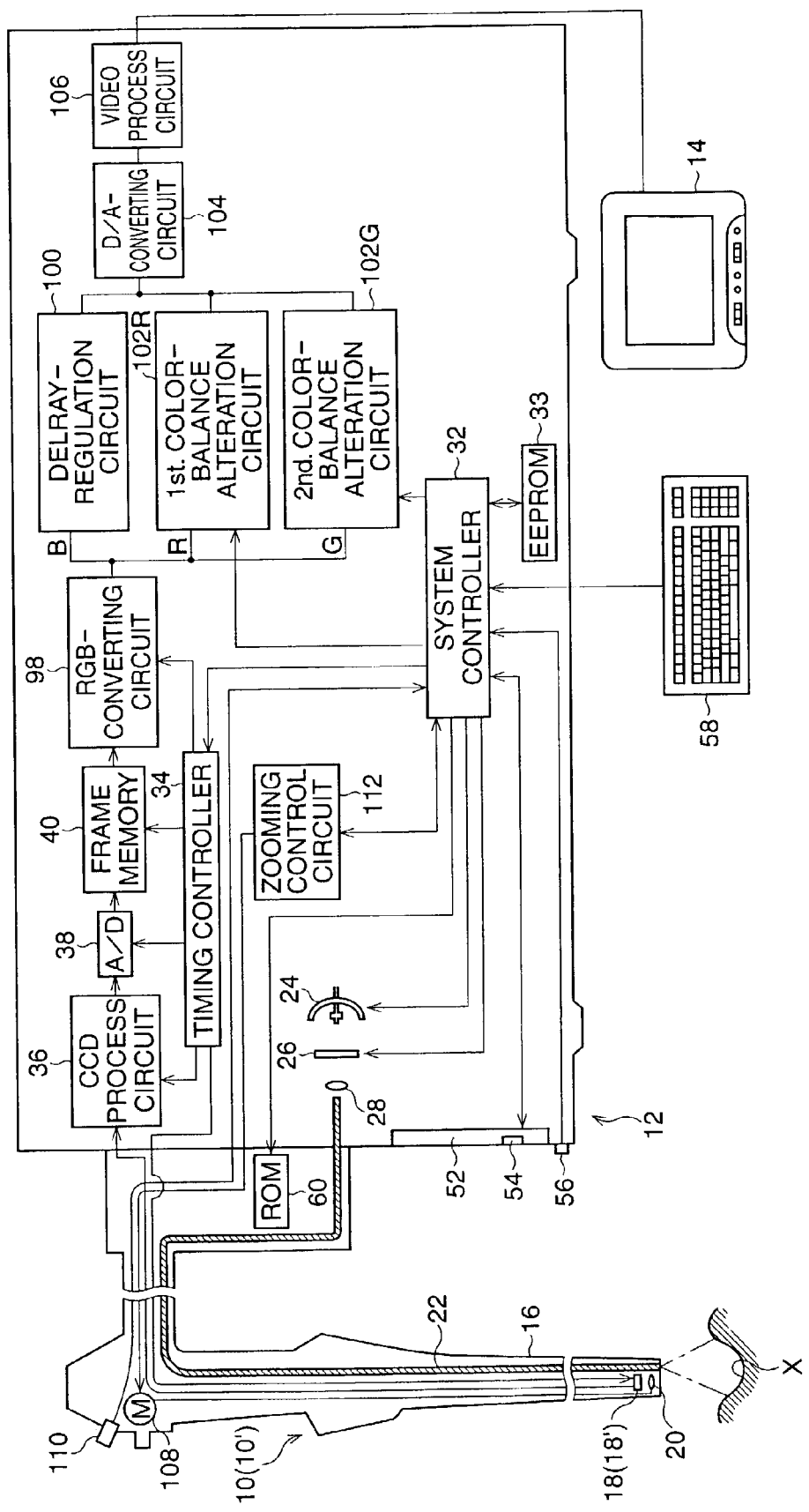
FIG. 26 is a schematic block diagram of a second embodiment of an electronic endoscope system according to the invention.

Referring to FIG. 26, a second embodiment of an electronic endoscope system according to the present invention is shown as a block diagram. In this drawing, the features similar to those of FIG. 1 are indicated by the same references.

In the second embodiment, an on-chip color filter method is introduced to reproduce an endoscope image as a full color image on a TV monitor 14. Namely, two types of video scopes 10 and 10' are respectively provided with CCD image sensors 18 and 18', each of which has a complementary color filter provided on a light-receiving surface thereof. Note, similar to the first embodiment, the CCD image sensor 18 features m×n image-pixel signals, and the CCD image sensor 18' features M×N image-pixel signals (M>m, N>n).

In the second embodiment, an image-signal processing unit 12 is constituted so as to conform to the on-chip color filter method as discussed hereinafter.

First, a light source device, provided in the image-signal processing unit 12, is formed by a white light lamp 24, a diaphragm 26, and a condenser lens 28. Namely, a rotary color-filter, indicated by reference 30 in FIG. 1, is eliminated from the light source device. Thus, white light is irradiated as an illuminating-light from a distal end face of an optical light guide 22. An illuminated object is focused as an optical endoscope image on the light-receiving surface of the CCD image sensor (18, 18') through the complementary color filter by an objective lens system 20, and the focused endoscope image is converted into a frame of color analog image-pixel signals due to the existence of the complementary color filter.

In the second embodiment, the image-signal processing unit 12 is also provided with a system controller 32 which controls the electronic endoscope system as a whole. Similar to the first embodiment, the system controller 32 contains a microcomputer comprising a central processing unit (CPU), a read-only memory (ROM) for storing programs and constants, a random-access memory (RAM) for storing temporary data, and an input/output interface circuit (I/O). Also, the system controller 32 is provided with a non-volatile memory or an electrically erasable programmable read-only memory (EEPROM) 33 for storing and keeping various data.

The image-signal processing unit 12 is further provided with a timing controller 34, which outputs various series of clock pulses having given frequencies under the control of the system controller 32, thereby operating sequentially and systematically the aforesaid image-signal processor provided in the image-signal processing unit 12. Of course, the timing controller 34 produces the various series of clock pulses having given frequencies, based on pixel-number data obtained from a read-only memory (ROM) 60 of either the video scope 10 or the video scope 10'.

In the second embodiment, the image-signal processor includes a CCD process circuit 36, an analog-to-digital (A/D) converter 38, a frame memory 40, a RGB-converting circuit 98, a delay-regulation circuit 100, a first color-balance alteration circuit 102R, a second color-balance alteration circuit 102G, a digital-to-analog (D/A) converting circuit 104, and a video process circuit 106.

Similar to the first embodiment, when the connection between the video scope 10 and the image-signal processing unit 12 is established, the CCD image sensor 18 is connected to the timing controller 34 and the CCD process circuit 36. The timing controller 34 produces and outputs a series of reading clock pulses to the CCD image sensor 18, whereby the frame of color analog image-pixel signals is sequentially and successively read from the CCD image sensor 18. The read color analog image-pixel signals are fed to the CCD process circuit 36, in which the color analog image-pixel signals are subjected to various image-processings, such as gamma-correction, white-balance correction, profile-enhancing, noise-elimination, black-level-clamping and so on. For these various image-processings, the CCD process circuit 36 is operated in accordance with various series of clock pulses output from the timing controller 34.

Each of the processed analog image-pixel signals is output from the CCD process circuit 36 to the A/D converter 38, in which the analog image-pixel signal concerned is converted into a digital image-pixel signal. The A/D converter 38 successively outputs color digital image-pixel signals, which are temporarily stored in the frame memory 40. The color digital image-pixel signals are successively read from the frame memory 40, and are then fed to the RGB-converting circuit 98, in which the color digital image-pixel signals are processed to thereby produce a red digital image-pixel signal, a green digital image-pixel signal, and a blue digital image-pixel signal. The respective red, green, and blue digital image-pixel signals R, G, and B are simultaneously output from the RGB-converting circuit 98 to the delay-regulation circuit 100, the first color-balance alteration circuit 102R, and the second color-balance alteration circuit 102G.

The first and second color-balance alteration circuits 102R and 102G are substantially identical to each other, and each circuit (102R, 102G) is constituted in substantially the same manner as the color-balance alteration circuit 44 shown in FIGS. 3 and 4.

When the simulated dye-spraying display mode is selected, the frames of red and green digital image-pixel signals are subjected to color-balance alteration processes in the first and second color-balance alteration circuits 102R and 102G, in substantially the same manner as in the color-balance alteration circuit 44. On the other hand, when a usual display mode is selected, the frames of red and green digital image-pixel signals can pass through the first and second color-balance alteration circuits 102R and 102G without being subjected to any color-balance alteration processes. Namely, during the selection of the usual display mode, a setting of "0" is used for a density factor "df" in both the first and second color-balance alteration circuits 102R and 102G.

The delay-regulation circuit 100 outputs a blue digital image-pixel signal after the time necessary for processing respective red and green digital image-pixel signals in the first and second color-balance alteration circuits 102R and 102G has elapsed. Namely, the outputting of the blue digital image-pixel signal from the delay-regulation circuit 100 is delayed for the processing time of the respective red and green digital image-pixel signals in both the first and second color-balance alteration circuits 102R and 102G. Thus, the respective blue, red, and green image-pixel signals are simultaneously output from the delay-regulation circuit 100, and the first and second color-balance alteration circuits 102R and 102G to the D/A converter 104.

The red, green and blue digital image-pixel signals are simultaneously converted into red, green, and blue analog image signals by the D/A converting circuit 104, and the red, green, and blue analog image signals are output to the video process circuit 106. Although not shown in FIG. 26, the timing controller 34 produces a composite synchronizing signal, and the composite synchronizing signal is output from the timing controller 34 to the video process circuit 106. Thus, the video process circuit 106 produces a component type video signal based on the red, green, and blue analog image signals output from the D/A converting circuit 104 and the composite synchronizing signal output from the timing controller 34.

Thus, during the selection of the usual display mode, an endoscope image, captured by the CCD image sensor 18, is reproduced as a full color motion picture on the TV monitor 14 with a given proper color balance in accordance with the component type video signal. On the other hand, during the selection of the simulated dye-spraying display mode, the endoscope image is reproduced on the TV monitor 14 as if it were sprayed with a blue-solution.

Similar to the first embodiment, although an electronic zooming system may be introduced in the image-signal processor provided in the image-signal processing unit 12, an optical zooming system is substituted for the electronic zooming system in the second embodiment.

In particular, the video scope (10, 10') features the optical zooming system incorporated in the objective lens system 20, and the optical zooming system is remotely operated by a zooming motor 108, such as stepping motor, provided in a manipulating section of the video scope (10, 10') as symbolically shown in FIG. 26. Also, the video scope (10, 10') features a zooming lever switch 110 provided on the manipulating section thereof. On the other hand, the image-signal processing unit 12 features a zooming control circuit 112 which is operated under the control of the system controller 32.

When a connection is established between the video scope (10, 10') and the image-signal processing unit 12, the zooming motor 108 is connected to the system controller 32 through the zooming-control circuit 112, and the zooming lever switch 110 is connected to the system controller 32. The zooming-control circuit 112 outputs a series of drive clock pulses to the zooming motor 108 under the control of the system controller 32, whereby the driving of the zooming motor 108 is controlled by the system controller 32. The zooming-lever switch 110 is constituted such that the zooming-motor 108 is rotationally driven in either a first drive direction or a second drive direction. When the zooming motor 108 is rotationally driven in the first drive direction, the optical zooming system is operated in a zoom-in manner. On the other hand, when the zooming motor 108 is rotationally driven in the second drive direction, the optical zooming system is operated in a zoom-out manner.

In the second embodiment, the optical zooming system features a magnifying power range between a magnifying power of "1" and a magnifying power of "4". During the operation of the optical zooming system, the number of drive clock pulses, output from the zooming control circuit 112 to the zooming motor 108, is counted by the system controller 32, and thus it is possible for the system controller 32 to recognize a magnifying power "mp" attained by the operation of the optical zooming system.

In the second embodiment, when the video scope 10' (M×N) is utilized, any one of the first, third, fifth, and seventh factor-setting modes is selected from the "FACTOR-SETTING TABLE" of FIG. 7 in accordance with the magnitude of the magnifying power "mp" attained by the operation of the optical zooming system of the video scope 10', as shown in the "FACTOR-SETTING-MODE SELECTION TABLE" of FIG. 27. Similarly, when the video scope 10 (m×n) is utilized, any one of the second, fourth, sixth, and eighth factor-setting modes is selected from the "FACTOR-SETTING TABLE" of FIG. 7 in accordance with a magnitude of the magnifying power "mp" attained by the operation of the optical zooming system of the video scope 10, as shown in the "FACTOR-SETTING-MODE SELECTION TABLE" of in FIG. 27.

The second embodiment is operated in generally the same manner as the first embodiment. In particular, the initialization routine, executed in the second embodiment, is substantially identical to the initialization routine of FIG. 11 Also, the respective routines, as shown in FIGS. 22, 23, and 24, are executed in substantially the same manner as the first embodiment.

Figure 28:
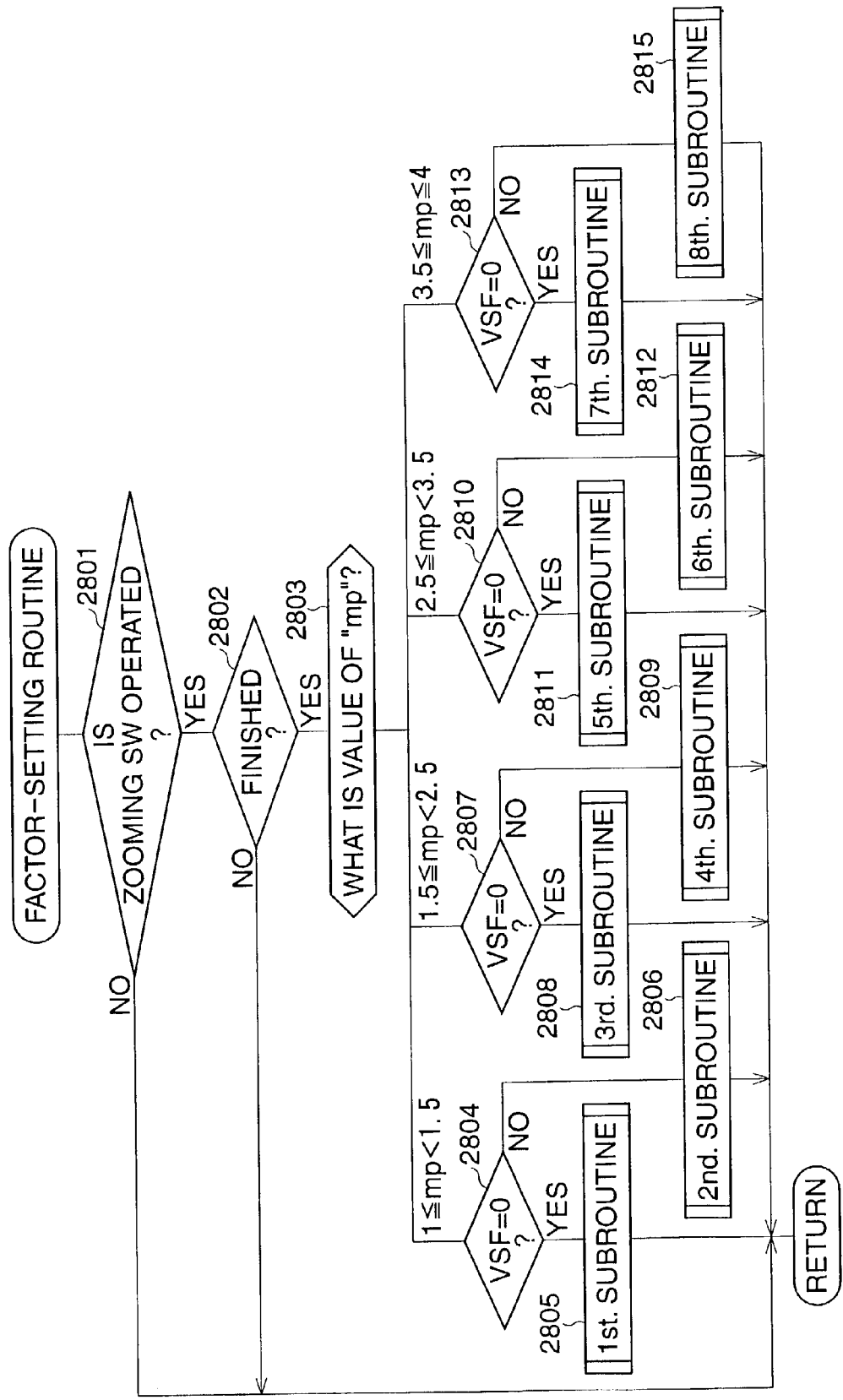
FIG. 28 is a flowchart of a factor-setting routine executed in a system controller of the image-signal processing unit shown in FIG. 26.

FIG. 28 shows a flowchart of a factor-setting routine executed in the system controller 32 used in the second embodiment. This routine is formed as a time-interruption routine executed at regular suitable intervals of, for example, 20 ms. The execution of the factor-setting routine is started after the execution of the initialization routine is completed.

At step 2801, it is monitored whether the zooming switch 108 has been operated. When the operation of the zooming switch 108 is not confirmed, the routine immediately ends. Thereafter, although the routine is repeatedly executed every 20 ms, there is no progress until the operation of the zooming switch 108 is confirmed.

At step 2801, when the operation of the zooming switch 108 is confirmed, the control proceeds to step 2802, in which it is monitored whether the operation of the zooming switch 108 has been finished. When the finish of the operation of the zooming switch 108 is confirmed, the control proceeds to step 2803, in which it is determined what the value of the magnifying power "mp", attained by the operation of the optical zooming system, is.

At step 2803, if the attained magnifying power "mp" falls within a range of 1≦mp<1.5, the control proceeds to step 2804, in which it is determined whether the video-scope-indication flag VSF is either "0" or "1".

If VSF=0, i.e. if the video scope 10', featuring M×N image-pixel signals, is used, the control proceeds to step 2805, in which a first subroutine is executed. The first subroutine is substantially identical to that of FIG. 14. Namely, the timing controller 34 produces and outputs the various series of clock pulses having given frequencies, based on the pixel-number data (M×N), whereby the frame of M×N color image-pixel signals, obtained from the video scope 10' (M×N), can be properly processed in the image-signal processor (step 1401 in FIG. 14). Then, in both the first and second color-balance alteration circuits 102R and 102G, factors f01 to f10 are set in accordance with the first factor-setting mode (1st. MODE), as shown in the "FACTOR-SETTING TABLE" of FIG. 7 (step 1402 in FIG. 14).

At step 2804, if VSF=1, i.e. if the video scope 10, featuring m×n image-pixel signals, is used, the control proceeds from step 2804 to step 2806, in which a second subroutine is executed. The second subroutine is substantially identical to that of FIG. 15. Namely, the timing controller 34 produces and outputs the various series of clock pulses having given frequencies, based on the pixel-number data (m×n), whereby the frame of m×n color image-pixel signals, obtained from the video scope 10 (m×n), can be properly processed in the image-signal processor (step 1501 in FIG. 15). Then, in both the first and second color-balance alteration circuits 102R and 102G, the factors f01 to f10 are set in accordance with a second factor-setting mode (2nd. MODE), as shown in the "FACTOR-SETTING TABLE" of FIG. 7 (step 1502 in FIG. 15).

At step 2803, if the attained magnifying power "mp" falls within a range of $1.5 \leq mp < 2.5$, the control proceeds to step 2807, in which it is determined whether the video-scope-indication flag VSF is either "0" or "1".

If VSF=0, i.e. if the video scope 10', featuring M×N image-pixel signals, is used, the control proceeds to step 2808, in which a third subroutine is executed. The third subroutine is substantially identical to the third subroutine of FIG. 16 except that step 1601 is replaced by step 1401 of FIG. 14. Namely, in both the first and second color-balance alteration circuits 102R and 102G, the factors f01 to f10 are set in accordance with a third factor-setting mode (3rd. MODE), as shown in the "FACTOR-SETTING TABLE" of FIG. 7 (step 1602 in FIG. 16).

At step 2807, if VSF=1, i.e. if the video scope 10, featuring m×n image-pixel signals, is used, the control proceeds from step 2807 to step 2809, in which a fourth subroutine is executed. The fourth subroutine is substantially identical to the fourth subroutine of FIG. 17 except that step 1701 is replaced by step 1501 in FIG. 15. Namely, in both the first and second color-balance alteration circuits 102R and 102G, the factors f01 to f10 are set in accordance with a fourth factor-setting mode (4th. MODE), as shown in the "FACTOR-SETTING TABLE" of FIG. 7 (step 1702 in FIG. 17).

At step 2803, if the attained magnifying power "mp" falls within a range of $2.5 \leq mp < 3.5$, the control proceeds to step 2810, in which it is determined whether the video-scope-indication flag VSF is either "0" or "1".

If VSF=0, i.e. if the video scope 10', featuring M×N image-pixel signals, is used, the control proceeds to step 2811, in which a fifth subroutine is executed. The fifth subroutine is substantially identical to the fifth subroutine of FIG. 18 except that step 1801 is replaced by step 1401 of FIG. 14. Namely, in both the first and second color-balance alteration circuits 102R and 102G, the factors f01 to f10 are set in accordance with a fifth factor-setting mode (5th. MODE), as shown in the "FACTOR-SETTING TABLE" of FIG. 7 (step 1802 in FIG. 18).

At step 2810, if VSF=1, i.e. if the video scope 10, featuring m×n image-pixel signals, is used, the control proceeds from step 2810 to step 2812, in which a sixth subroutine is executed. The sixth subroutine is substantially identical to the sixth subroutine of FIG. 19 except that step 1901 is replaced by step 1501 of FIG. 15. Namely, in both the first and second color-balance alteration circuits 102R and 102G, the factors f01 to f10 are set in accordance with a sixth factor-setting mode (6th. MODE), as shown in the "FACTOR-SETTING TABLE" of FIG. 7 (step 1902 in FIG. 19).

At step 2803, if the attained magnifying power "mp" falls within a range of $3.5 \leq p < 4$, the control proceeds to step 2813, in which it is determined whether the video-scope-indication flag VSF is either "0" or "1".

If VSF=0, i.e. if the video scope 10', featuring M×N image-pixel signals, is used, the control proceeds to step 2814, in which a seventh subroutine is executed. The seventh subroutine is substantially identical to the seventh subroutine of FIG. 20 except that step 2001 is replaced by step 1401 of FIG. 14. Namely, in both the first and second color-balance alteration circuits 102R and 102G, the factors f01 to f10 are set in accordance with a seventh factor-setting mode (7th. MODE), as shown in the "FACTOR-SETTING TABLE" of FIG. 7 (step 2002 in FIG. 20).

At step 2813, if VSF=1, i.e. if the video scope 10, featuring m×n image-pixel signals, is used, the control proceeds from step 2813 to step 2815, in which an eighth subroutine is executed. The eighth subroutine is substantially identical to the eighth subroutine of FIG. 21 except that step 2101 is replaced by step 1501 of FIG. 15. Namely, in both the first and second color-balance alteration circuits 102R and 102G, the factors f01 to f10 are set in accordance with an eighth factor-setting mode (8th. MODE), as shown in the "FACTOR-SETTING TABLE" of FIG. 7 (step 2102 in FIG. 21).

Figure 29:
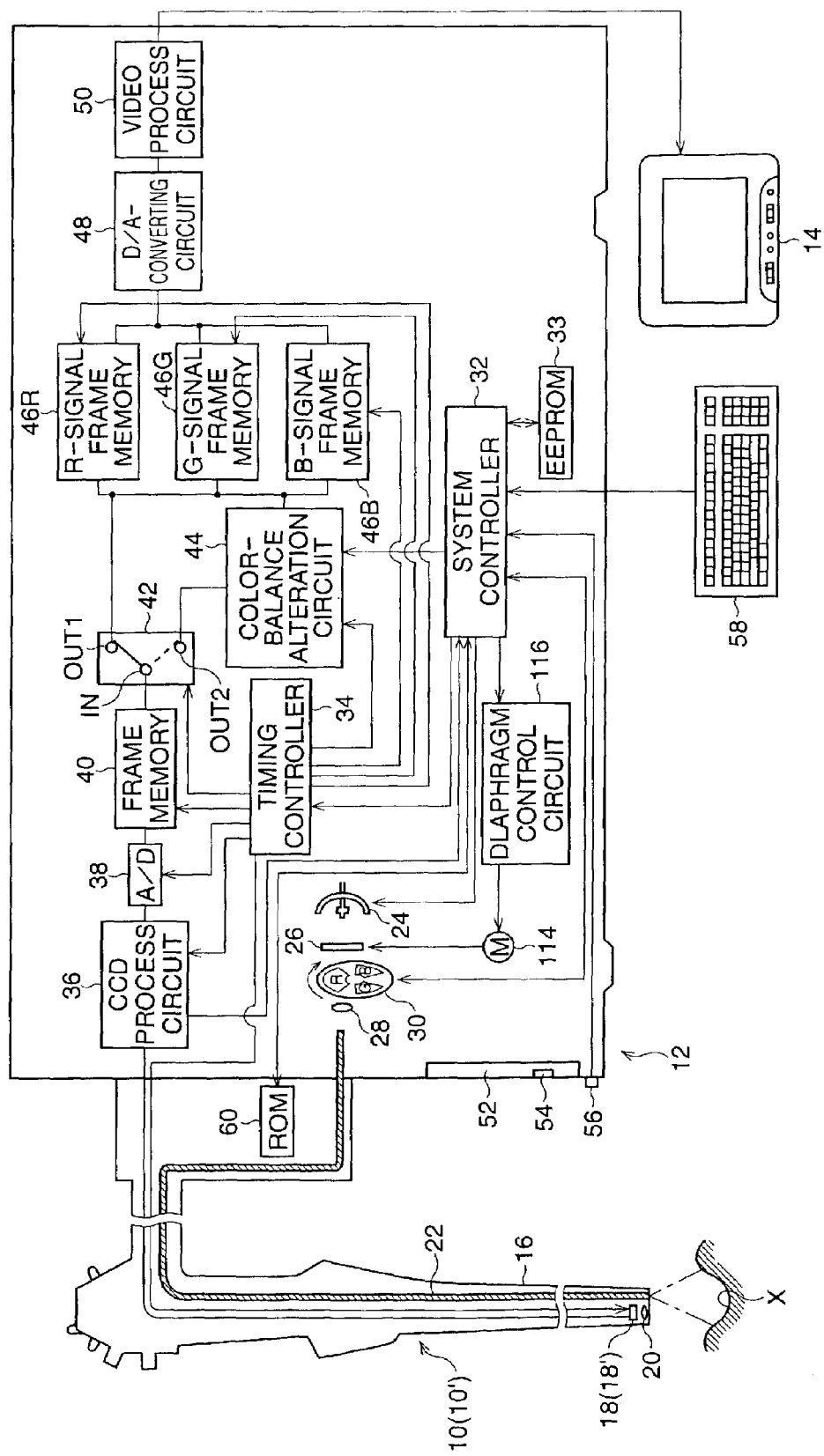
FIG. 29 is a schematic block diagram of a third embodiment of an electronic endoscope system according to the invention.

Referring to FIG. 29, a third embodiment of an electronic endoscope system according to the present invention is shown as a block diagram. The third embodiment is essentially identical to the first embodiment except that the electronic zooming system is eliminated from the image-signal processor provided in the image-signal processing unit 12. In this drawing, the features similar to those of FIG. 1 are indicated by the same references.

In general, in an electronic endoscope system, an objective lens system, used in a video scope, features a large depth of focus, because a close-range object image and/or a distant-range object image to be captured by a CCD image sensor must be focused on a light-receiving surface of the CCD image sensor by the objective lens system, before the captured close-range object image and/or distant-range object image can be sharply reproduced on a TV monitor.

In this case, to maintain a constant overall luminance of a reproduced object image or endoscope image on the TV monitor, radiation of an illuminating-light from a distal end of an optical light guide should be regulated in accordance with a distance between the captured endoscope image and the distal end of the video scope. For example, when an uneven surface of the mucous membrane of a stomach is to be reproduced as a maximum close-up image by placing the distal end of the video scope close to the uneven surface of mucous membrane, the radiation of the illuminating-light should be lowered to a minimum level in order to generate the endoscope image at a predetermined luminance on the TV monitor.

As the distal end of the video scope is gradually moved away from the uneven surface of the mucous membrane, the radiation of the illuminating-light should be increased from the minimum level to thereby prevent the luminance of the reproduced endoscope image from being reduced. In this case, a spatial frequency of the endoscope image captured by the CCD image sensor gradually becomes lower. Thus, in a case where a color-balance alteration process is introduced in the electronic endoscope, the distance between the uneven surface of the mucous membrane and the distal end of the video scope should be taken into account, before a color-balance alteration process can be properly performed.

The third embodiment is constituted so as to cope with a variation of the spatial frequency of the endoscope image in accordance with the change in distance between the distal end of the video scope (10, 10') and the uneven surface of the mucous membrane of, for example, a stomach or a colon.

In FIG. 29, reference 114 indicates a diaphragm motor, such as a stepping motor, for actuating the diaphragm 26 to regulate the amount of illuminating-light directed from the lamp 24 to the proximal end of the light guide 22, and reference 116 indicates a diaphragm-control circuit for driving the diaphragm motor 114.

The diaphragm-control circuit 116 outputs a series of drive clock pulses to the diaphragm motor 114 under the control of the system controller 32, whereby the driving of the diaphragm motor 114 is controlled by the system controller 32, such that a constant overall luminance of a reproduced endoscope image on the TV monitor 14 can be maintained. During the actuation of the diaphragm 26, the number of drive clock pulses, output from the diaphragm-control circuit 116 to the diaphragm motor 114, is counted by the system controller 32, and thus it is possible for the system controller 32 to recognize an opening value "ov" attained by the actuation of the diaphragm 26.

The larger the opening value "ov", the larger the amount of the illuminating-light directed from the lamp 24 to the proximal end of the light guide 22. Also, as is apparent from the foregoing, the opening value "ov" represents the distance between the distal end of the video scope (10, 10') and the uneven surface of mucous membrane of, for example, a stomach or a colon. Namely, the larger the opening value "ov", the larger the distance from the distal end of the video scope (10, 10') to the uneven surface to the mucous membrane.

In the third embodiment, when the video scope 10' (M×N) is utilized, any one of the first, third, fifth, and seventh factor-setting modes is selected from the "FACTOR-SETTING TABLE" of FIG. 7 in accordance with the magnitude of the opening value "ov" which is calculated from the counted number of drive clock pulses output from the diaphragm-control circuit 116 to the diaphragm motor 114, as shown in the "FACTOR-SETTING-MODE SELECTION TABLE" of in FIG. 30. Similarly, when the video scope 10 (m×n) is utilized, any one of the second, fourth, sixth, and eighth factor-setting modes is selected from the "FACTOR-SETTING TABLE" of FIG. 7 in accordance with a magnitude of the opening value "ov" which is calculated from the counted number of drive clock pulses output from the diaphragm-control circuit 116 to the diaphragm motor 114, as shown in the "FACTOR-SETTING-MODE SELECTION TABLE" of FIG. 30.

In the "FACTOR-SETTING-MODE SELECTION TABLE" of FIG. 30, references "$OV_{MIN}$", "$OV_1$", "$OV_2$", and "$OV_3$" represent constant opening values of the diaphragm 26. When the diaphragm 26 exhibits the minimum opening value "$OV_{MIN}$", an uneven surface of the mucous membrane of, for example, a stomach or a colon is reproduced as a maximum close-up endoscope image on the TV monitor 14 by placing the distal end of the video scope (10, 10') close to the uneven surface of the mucous membrane. The opening value "$OV_1$", "$OV_2$", and "$OV_3$" are larger than the minimum opening value "AVMIN", and are suitably selected. Note, as is apparent from FIG. 30, there is a relationship of $OV_1 < OV_2 < OV_3$.

As mentioned above, in the third embodiment, the optical zooming system is not introduced into the video scope (10, 10'), the zoom-in and zoom-out switches 82 and 84, the zooming-level indicator 86, and the initialization switch 88 are eliminated from the front panel 52, and the second LED driver circuit 96 and the LED's ($ZD_1$ to $ZD_4$) are also eliminated.

The third embodiment is operated in generally the same manner as the first embodiment. In particular, in the third embodiment, an initialization routine, executed in the third embodiment, is substantially identical to the initialization routine of FIG. 11, except that steps 1109 and 1110 are eliminated therefrom. Also, the respective routines, as shown in FIGS. 22, 23, and 24, are executed in substantially the same manner as in the first embodiment.

Figure 31:
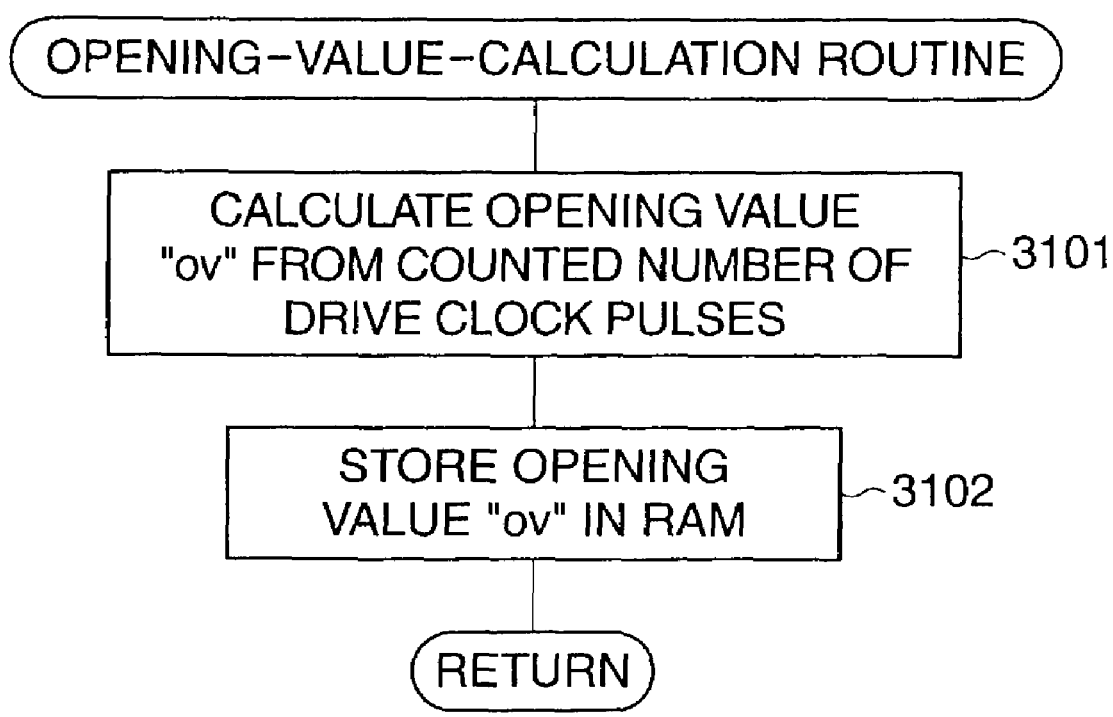
FIG. 31 is a flowchart of an opening-value-calculation routine executed in a system controller of the image-signal processing unit shown in FIG. 29.

FIG. 31 shows a flowchart of an opening-value calculation routine executed in the system controller 32 used in the third embodiment. This routine is formed as a time-interruption routine executed at regular suitable intervals of, for example, 100 ms. The execution of the calculation routine is started after the execution of the initialization routine is completed.

At step 3101, an opening value "ov" is calculated from the counted number of drive clock pulses output from the diaphragm-control circuit 116 to the diaphragm motor 114. Then, at step 3102, the calculated opening value "ov" is stored in the RAM of the system controller 32. Namely, the opening value "ov" is renewed every 100 ms.

Figure 32:
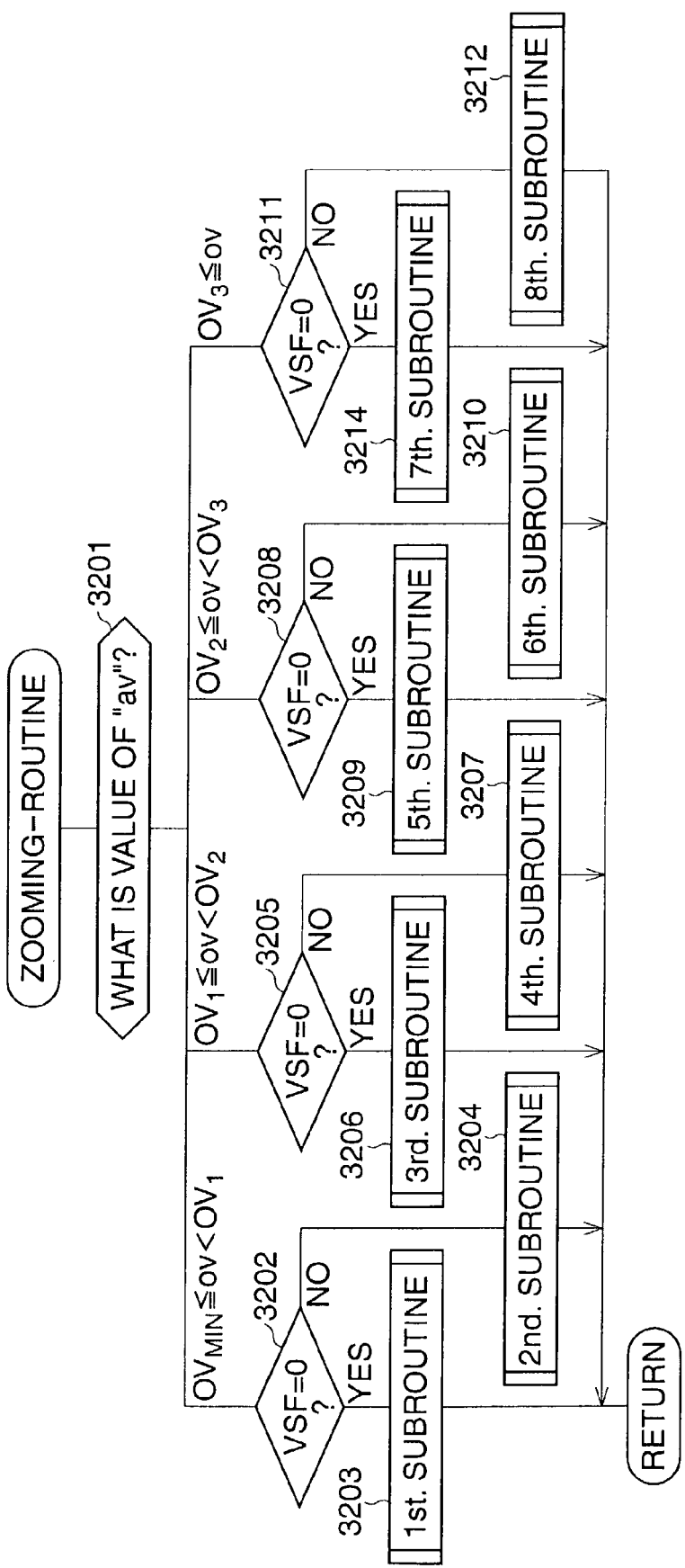
FIG. 32 is a flowchart of a factor-setting routine executed in the system controller of the image-signal processing unit shown in FIG. 29.

FIG. 32 shows a flowchart of a factor-setting routine executed in the system controller 32 used in the third embodiment. This routine is formed as a time-interruption routine executed at regular suitable intervals of, for example, 20 ms. The execution of the factor-setting routine is started after the execution of the initialization routine is completed.

At step 3201, it is determined what the opening value "ov", calculated in the opening-value calculation routine, is.

If the calculated opening value "ov" falls within a range of $OV_{MIN} \leq ov < OV_1$, the control proceeds to step 3202, in which it is determined whether the video-scope-indication flag VSF is either "0" or "1".

If VSF=0, i.e. if the video scope 10', featuring M×N image-pixel signals, is used, the control proceeds to step 3203, in which a first subroutine is executed. The first subroutine is substantially identical to that of FIG. 14. Namely, the timing controller 34 produces and outputs the various series of clock pulses having given frequencies, based on the pixel-number data (M×N), whereby the frame of M×N color image-pixel signals, obtained from the video scope 10' (M×N), can be properly processed in the image-signal processor (step 1401 in FIG. 14). Then, in the color-balance alteration circuit 44, the factors f01 to f10 are set in accordance with a first factor-setting mode (1st. MODE), as shown in the "FACTOR-SETTING TABLE" of FIG. 7 (step 1402 in FIG. 14).

At step 3202, if VSF=1, i.e. if the video scope 10, featuring m×n image-pixel signals, is used, the control proceeds from step 3202 to step 3204, in which a second subroutine is executed. The second subroutine is substantially identical to that of FIG. 15. Namely, the timing controller 34 produces and outputs the various series of clock pulses having given frequencies, based on the pixel-number data (m×n), whereby the frame of m×n color image-pixel signals, obtained from the video scope 10 (m×n), can be properly processed in the image-signal processor (step 1501 in FIG. 15). Then, in the color-balance alteration circuit 44, the factors f01 to f10 are set in accordance with a second factor-setting mode (2nd. MODE), as shown in the "FACTOR-SETTING TABLE" of FIG. 7 (step 1502 in FIG. 15).

At step 3201, if the calculated opening value "ov" falls within a range of $OV_1 \leq ov < OV_2$, the control proceeds to step 3205, in which it is determined whether the video-scope-indication flag VSF is either "0" or "1".

If VSF=0, i.e. if the video scope 10', featuring M×N image-pixel signals, is used, the control proceeds to step 3206, in which a third subroutine is executed. The third subroutine is substantially identical to the third subroutine of FIG. 16 except that step 1601 is replaced by step 1401 of FIG. 14. Namely, in the color-balance alteration circuit 44, the factors f01 to f10 are set in accordance with a third factor-setting mode (3rd. MODE), as shown in the "FACTOR-SETTING TABLE" of FIG. 7 (step 1602 in FIG. 16).

At step 3205, if VSF=1, i.e. if the video scope 10, featuring m×n image-pixel signals, is used, the control proceeds from step 3205 to step 3207, in which a fourth subroutine is executed. The fourth subroutine is substantially identical to the fourth subroutine of FIG. 17 except that step 1701 is replaced by step 1501 of FIG. 15. Namely, in the color-balance alteration circuit 44, the factors f01 to f10 are set in accordance with a fourth factor-setting mode (4th. MODE), as shown in the "FACTOR-SETTING TABLE" of FIG. 7 (step 1702 in FIG. 17).

At step 3201, if the calculated opening value "ov" falls within a range of $OV_2 \leq ov < OV_3$, the control proceeds to step 3208, in which it is determined whether the video-scope-indication flag VSF is either "0" or "1".

If VSF=0, i.e. if the video scope 10', featuring M×N image-pixel signals, is used, the control proceeds to step 3209, in which a fifth subroutine is executed. The fifth subroutine is substantially identical to the fifth subroutine of FIG. 18 except that step 1801 is replaced by step 1401 of FIG. 14. Namely, in the color-balance alteration circuit 44, the factors f01 to f10 are set in accordance with a fifth factor-setting mode (5th. MODE), as shown in the "FACTOR-SETTING TABLE" of FIG. 7 (step 1802 in FIG. 18).

At step 3208, if VSF=1, i.e. if the video scope 10, featuring m×n image-pixel signals, is used, the control proceeds from step 3208 to step 3210, in which a sixth subroutine is executed. The sixth subroutine is substantially identical to the sixth subroutine of FIG. 19 except that step 1901 is replaced by step 1501 of FIG. 15. Namely, in the color-balance alteration circuit 44, the factors f01 to f10 are set in accordance with a sixth factor-setting mode (6th. MODE), as shown in the "FACTOR-SETTING TABLE" of FIG. 7 (step 1902 in FIG. 19).

At step 3201, if the calculated opening value "ov" falls within a range of $OV_3 \leq ov$, the control proceeds to step 3211, in which it is determined whether the video-scope-indication flag VSF is either "0" or "1".

If VSF=0, i.e. if the video scope 10', featuring M×N image-pixel signals, is used, the control proceeds to step 3214, in which a seventh subroutine is executed. The seventh subroutine is substantially identical to the seventh subroutine of FIG. 20 except that step 2001 is replaced by step 1401 of Fig. Namely, in the color-balance alteration circuit 44, the factors f01 to f10 are set in accordance with a seventh factor-setting mode (7th. MODE), as shown in the "FACTOR-SETTING TABLE" of FIG. 7 (step 2002 in FIG. 20).

At step 3211, if VSF=1, i.e. if the video scope 10, featuring m×n image-pixel signals, is used, the control proceeds from step 3211 to step 3212, in which an eighth subroutine is executed. The eighth subroutine is substantially identical to the eighth subroutine of FIG. 21 except that step 2101 is replaced by step 1501 of FIG. 15. Namely, in the color-balance alteration circuit 44, the factors f01 to f10 are set in accordance with an eighth factor-setting mode (8th. MODE), as shown in the "FACTOR-SETTING TABLE" of FIG. 7 (step 2102 in FIG. 21).

Finally, it will be understood by those skilled in the art that the foregoing description is of preferred embodiments of the system, and that various changes and modifications may be made to the present invention without departing from the spirit and scope thereof.

The present disclosure relates to subject matters contained in Japanese Patent Application No. 2001-193308 (filed on Jun. 26, 2001), which is expressly incorporated herein, by reference, in its entirety.

What is claimed is:

1. An electronic endoscope system including a video scope having a solid-state image sensor that successively produces a frame of color image-pixel signals, and an image-signal processor that produces a color video signal based on said frame of color image-pixel signals, said electronic endoscope system comprising:
   a calculator that calculates a difference value between a value of a central single-color image-pixel signal and an average of values of some circumferential single-color image- pixel signals selected from single-color image-pixel signals surrounding said central single-color image-pixel signal;
   a color-balance alteration system that alters the value of said central single-color image-pixel signal based on the difference value calculated by said calculator; and
   a selector that selects said circumferential single-color image-pixel signals such that the distance between the circumferential single-color image-pixel signals to be selected and said central single-color image-pixel signal increases as a spatial frequency of an endoscope image to be reproduced based on said color video signal decreases.

2. An electronic endoscope system as set forth in claim 1, wherein said calculator further includes a multiplier that multiplies said difference value by a density factor, and the alteration of the value of said central single-color image-pixel signal by said color-balance alteration system is performed based on the multiplied difference value.

3. An electronic endoscope system as set forth in claim 1, wherein the color-balance alteration system further includes:
   a determiner that determines whether the value of said central single-color image-pixel signal is lower than said average of values; and
   a subtractor that subtracts the absolute value of the difference value from the value of said central single-color image-pixel signal when it is determined by said determiner that the value of said central single-color image-pixel signal is lower than said average of values, with the value of said central single-color image-pixel signal being unchanged when it is determined by said determiner that the value of said central single-color image-pixel signal is equal to or higher than said average of values.

4. An electronic endoscope system as set forth in claim 3, wherein the color-balance alteration system further includes a multiplier that multiplies the difference value by a factor, and the absolute value of the multiplied difference value is subtracted from the value of said central single-color image-pixel signal by said subtractor.

5. An electronic endoscope system as set forth in claim 1, wherein said selector is associated with an electronic zooming system introduced in said image-signal processor.

6. An electronic endoscope system as set forth in claim 5, wherein said selector is further associated with at least two video scopes featuring different types of solid-state image sensors, which produce different numbers of image-pixel signals in one frame.

7. An electronic endoscope system as set forth in claim 1, wherein said selector is associated with an optical zooming system introduced in said video scope.

8. An electronic endoscope system as set forth in claim 7, wherein said selector is further associated with at least two video scopes featuring different types of solid-state image sensors, which produce different numbers of image-pixel signals in one frame.

9. An electronic endoscope system as set forth in claim 1, further comprising a diaphragm system that maintains a constant overall luminance of the reproduced endoscope image, wherein said selector is associated with said diaphragm system.

10. An electronic endoscope system as set forth in claim 9, wherein said selector is further associated with at least two video scopes featuring different types of solid-state image sensors, which produce different numbers of image-pixel signals in one frame.

11. An electronic endoscope system as set forth in claim 5, wherein said spatial frequency varies due to a change of an enlarging rate of said electronic zooming system.

12. An electronic endoscope system as set forth in claim 7, wherein said spatial frequency varies due to a change of a magnifying power of said optical zooming system.

13. An electronic endoscope system as set forth in claim 9, wherein said spatial frequency varies due to a change of an opening value of said diaphragm system.

14. An electronic endoscope system as set forth in claim 1, wherein said selector is associated with at least two video scopes featuring different types of solid-state image sensors, which produce different numbers of image-pixel signals in one frame.

15. An electronic endoscope system as set forth in claim 14, wherein said spatial frequency varies due to a substitution of a different type of said video scope.

* * * * *